(12) United States Patent
Herdewijn et al.

(10) Patent No.: US 10,087,209 B2
(45) Date of Patent: Oct. 2, 2018

(54) ANTIVIRAL COMPOUNDS, A PROCESS FOR THEIR PREPARATION, AND THEIR USE FOR TREATING VIRAL INFECTIONS

(71) Applicant: KU LEUVEN RESEARCH & DEVELOPMENT

(72) Inventors: Piet Herdewijn, Heverlee (BE); Steven De Jonghe, Tervuren (BE); Shrivinas Dumbre, Leuven (BE); Chao Liu, Heverlee (BE)

(73) Assignee: KU LEUVEN RESEARCH & DEVELOPMENT, Leuven (BE)

( * ) Notice: Subject to any disclaimer, the term of this patent is extended or adjusted under 35 U.S.C. 154(b) by 0 days.

(21) Appl. No.: 15/568,692

(22) PCT Filed: Apr. 27, 2016

(86) PCT No.: PCT/EP2016/059394
§ 371 (c)(1),
(2) Date: Oct. 23, 2017

(87) PCT Pub. No.: WO2016/174081
PCT Pub. Date: Nov. 3, 2016

(65) Prior Publication Data
US 2018/0105552 A1    Apr. 19, 2018

(30) Foreign Application Priority Data

Apr. 28, 2015  (GB) .................................... 1507181.4
Jan. 25, 2016  (GB) .................................... 1601277.5

(51) Int. Cl.
| | | |
|---|---|---|
| C07H 19/10 | (2006.01) |
| C07H 19/20 | (2006.01) |
| A61K 31/7076 | (2006.01) |
| A61K 45/06 | (2006.01) |
| A61P 35/00 | (2006.01) |
| A61K 31/708 | (2006.01) |
| A61K 31/7072 | (2006.01) |
| A61K 31/7068 | (2006.01) |
| A61P 31/20 | (2006.01) |

(52) U.S. Cl.
CPC ........... *C07H 19/20* (2013.01); *A61K 31/708* (2013.01); *A61K 31/7068* (2013.01); *A61K 31/7072* (2013.01); *A61K 31/7076* (2013.01); *A61K 45/06* (2013.01); *A61P 31/20* (2018.01); *A61P 35/00* (2018.01); *C07H 19/10* (2013.01)

(58) Field of Classification Search
None
See application file for complete search history.

(56) References Cited

FOREIGN PATENT DOCUMENTS

| WO | 2005085268 | 9/2005 |
|---|---|---|
| WO | 03/093290 | 11/2013 |

OTHER PUBLICATIONS

Vina et al., Science Direct, Tetrahedron, 63, 2007, pp. 2634-2646.*
Pertusati et al., "Medicinal chemistry of nucleoside phosphonate prodrugs for aniviral therapy", Antiviral Chemistry & Chemotherapy, vol. 22, No. 5, 2012, pp. 181-203.
Pradere et al., "Synthesis of Nucleoside Phosphate and Phosphonate Prodrugs", American Chemical Society, vol. 114, No. 18, 2014, pp. 9154-9218.
Wu et al., "Deoxythreoslyl Phosphonate Nucleosides as Selecive Anti-HIV Agents", J. Am Chem. Soc., 127, 2005, pp. 5056-5065.
Schoning et al., "The a-L-Threofuranosyl-(3'-2')-oligonucleotide System ('TNA'): Synthesis and Pairing Properties", Helvetica Chimica Acta, Vol, 85, 2002, pp. 4111-4153.
Dumbre et al., "Synthesis of a-L-Threose Nucleoside Phosphates via Regioselective Sugar Protection", The Journal of Organic Chemistry, 78, 2013, pp. 7137-7144.
Mackman et al., "Discovery of GS-9131: Design, synthesis and optimization of amidate prodrugs of the novel nucleoside phosphonate HIV reverse transcriptase (RT) inhibitor GS-9148", Bioroganic and Medicinal Chemistry, 18, 2010, pp. 3606-3617.
Kiyokawa et al., "Synthesis of Cyclopropane-Containing Phosphorus Compounds by Radical Coupling of Butenylindium with Iodo Phosphorus Compounds", Eur. J. Org. Chem., 2011, pp. 2163-2171.
Vina et al., "Synthesis of 3'0-phuphonomethyl nucleosides with an adenine base moitey", Science Direct, Tetrahedron, 63, 2007, pp. 2634-2646.
Li et al., "A Convenient Synthesis of Amino Acid Methyl Esters", Molecules, 13, 2008, pp. 1111-1119.
Maiti et al., "Aspartic acid based nucleoside phosphoramidate prodrugs as potent inhibitors of hepatitis C virus replication", Org. Biomol. Chem., 13, 2015, pp. 5158-5174.

(Continued)

*Primary Examiner* — Traviss C McIntosh, III
(74) *Attorney, Agent, or Firm* — Duane Morris LLP; Gregory M. Lefkowitz; Jason M. Nolan

(57) ABSTRACT

The present invention relates to novel pro-drugs of L-2'-deoxythreose nucleoside phosphonates, such as phosphoramidate, phosphorodiamidate and phospho-diester pro-drugs. The invention also relates to a process for preparing these novel prodrugs of nucleoside phosphonates. The invention also relates to the use of these novel phosphonate-modified nucleosides to treat or prevent viral infections and their use to manufacture a medicine to treat or prevent viral infections, particularly infections with viruses belonging to the HBV family.

24 Claims, No Drawings

(56) References Cited

OTHER PUBLICATIONS

Korba et al., "A cell culture assay for compounds which inhibit hepatitis B virus replication", Antiviral Research, 15, 1991, pp. 217-228.
Korba et al., "Use of a standard cell culture assay to assess activities of nucleoside analogs against hepatitis B virus replication", Antiviral Research, 19, 1992, pp. 55-70.

\* cited by examiner

ANTIVIRAL COMPOUNDS, A PROCESS FOR THEIR PREPARATION, AND THEIR USE FOR TREATING VIRAL INFECTIONS

CROSS-REFERENCE TO RELATED APPLICATIONS

This application is a § 371 national stage entry of International Application No. PCT/EP2016/059394, filed Apr. 27, 2016, which claims priority to Great Britain Application No. 1507181.4, filed Apr. 28, 2015, and Great Britain Application No. 1601277.5, filed Jan. 25, 2016, the entire contents of which are incorporated herein by reference.

FIELD OF THE INVENTION

The present invention relates to novel prodrugs of L-2'-deoxythreose nucleoside phosphonates, such as phosphoramidate, phosphorodiamidate and phospho-diester prodrugs. The invention also relates to a process for preparing these novel prodrugs of nucleoside phosphonates. The invention also relates to the use of these novel phosphonate-modified nucleosides to treat or prevent viral infections and their use to manufacture a medicine to treat or prevent viral infections, particularly infections with viruses belonging to the HBV family.

BACKGROUND OF THE INVENTION

More than 350 million people are chronically infected with the hepadnavirus Hepatitis B (HBV). The spectrum of the disease is diverse and variable, ranging from an inactive carrier state to progressive chronic hepatitis B (CHB). However, in most HBV carriers, liver disease progresses through cirrhosis to hepatocellular carcinoma, leading to approximately 1 million deaths each year and currently represent 5-10% of cases of liver transplantation. Hence, the goal of drug therapy is to halt the progression of cirrhosis and to block the appearance of cancer. Current approaches for the treatment of Hepatitis B infections include interferon therapy and treatment with nucleoside analogues. Interferon therapy (either standard or pegylated) stimulates the hosts' antiviral immune response. Interferon must be given by parenteral administration and its use is associated with several side effects (such as influenza-like symptoms, anorexia and depression). The main goal of nucleoside analogue therapy is to block viral DNA synthesis and thereby reduce the number of infected hepatocytes. Currently, five nucleoside analogues have been licensed for the treatment of HBV infections. lamivudine (LMV), adefovir dipivoxil (ADV), entecavir, telbivudine, and tenofovir disoproxil fumarate (TDF) (FIG. 1). TFV and ETV are nowadays considered as first-line treatments because of their potent antiviral activity and their high barrier to resistance.

FIG. 1: FDA approved anti-HBV nucleosides and nucleotides

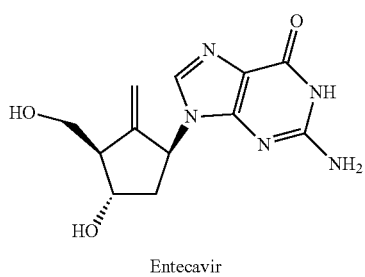

Entecavir

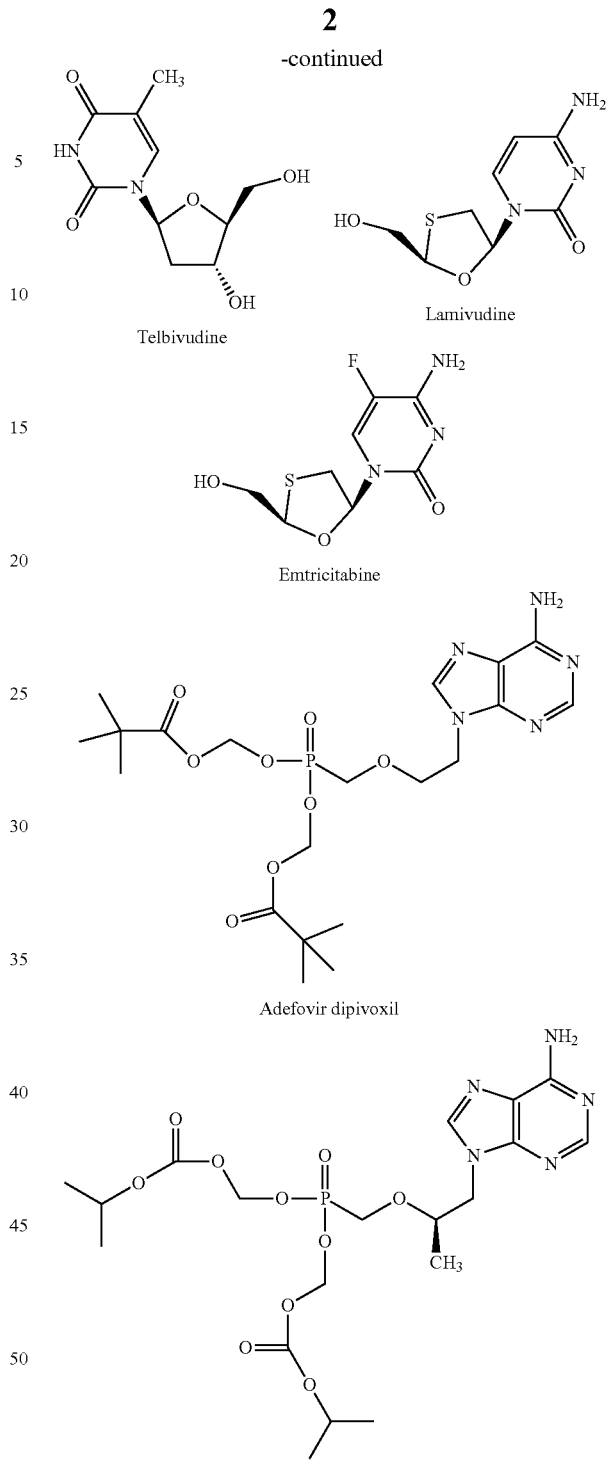

Telbivudine

Lamivudine

Emtricitabine

Adefovir dipivoxil

Tenofovir disoproxil

Lamivudine, entecavir and telbivudine are classical antiviral nucleosides, whose antiviral activity depends upon their intracellular metabolism within virus-infected cells to form sequentially the mono-, di- and triphosphates. It is these nucleotides, and especially the triphosphates that are the pharmacologically active species, as they are incorporated into a growing DNA strand by a DNA polymerase, resulting in chain termination or fraudulent DNA/RNA. The first phosphorylation step leading to the formation of the nucleoside 5'-monophosphate is commonly catalyzed by a nucleoside kinase encoded by the host cell or the virus infecting the host cell. Conversion of the nucleoside monophosphate to the corresponding 5'-diphosphate and triphosphates is carried out by nucleoside, nucleotide, and nucleoside diphosphate kinases, respectively. Hence, cellular kinases, as well as virally-encoded kinases play a vital role in the activation of nucleoside drugs.

Adefovir and Tenofovir are both nucleoside phosphonates, which can be considered as nucleoside monophosphate analogues, having the advantage of being metabolically stable, as the phosphorus-carbon bond is not susceptible to hydrolytic cleavage. Moreover, the presence of a phosphonate group allows the first phosphorylation step, required for nucleoside activation to be skipped, therefore bypassing the rate-limiting step in the conversion to the nucleoside-triphosphate. Although metabolically stable, phosphonates are negatively charged at physiological pH, and hence, are not able to penetrate the lipid-rich cell membrane, which hampers their antiviral activity. Therefore, these compounds are marketed as an orally bioavailable prodrug.

In order to bypass the first, rate-limiting phosphorylation step in the bioactivation of nucleosides, cyclic nucleoside phosphonates have been synthesized. An example includes a series of L-2'-deoxythreose nucleoside phosphonate analogues that have been synthesized (see *J. Am. Chem. Soc.* 2005, 127, 5056-5065). Two congeners showed excellent activity. PMDTA (phosphonomethoxydeoxythreosyl adenine) displayed an $EC_{50}$ value of 2.53 µM against both HIV-1 and HIV-2, whereas PMDTT (phosphonomethoxydeoxythreosyl thymine) was endowed with an $IC_{50}$ value of 6.59 µM against HIV-1 and HIV-2. In addition, these analogues lack cellular cytotoxicity ($CC_{50}$ values are >316 µM for PMDTA and >343 µM for PMDTT). Despite its promising antiviral profile, the highly charged nature of the phosphonate moiety hampers their cellular permeability.

The present invention is based on the unexpected finding that dome prodrugs of these PMDT show unexpected biological properties, in particular have significant antiviral activity against the Hepatitis B virus.

SUMMARY OF THE INVENTION

The present invention relates to novel prodrugs of phosphonomethoxydeoxythreosyl (PMDT) nucleoside phosphonates, and their use as agents for treating viral diseases. It is based on the unexpected finding that certain nucleoside prodrugs show unexpected biological properties, in particular have significant activity against the hepatitis B virus.

Numbered statements of the invention are:

1. A compound of formula I:

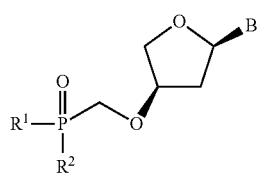

I wherein

B is any natural or modified nucleobase $R^1$ has the general formula II

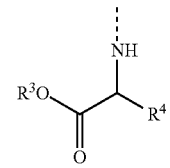

II wherein $R^3$ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

$R^4$ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl, X—$COOR^5$, X—OCO—$R^5$;

wherein X is aryl, heteroaryl, $C_1$-$C_{10}$ alkyl, $C_2$-$C_{10}$ alkenyl, $C_2$-$C_{10}$ alkynyl, or $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, halo-alkyl, cyano, $C_1$-$C_7$ alkoxy; and wherein $R^5$ is selected from the group consisting of aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

$R^2$ is O—Ar, wherein Ar is a fused bicyclic aryl moiety or a monocyclic aryl moiety, either of which aryl moieties is carbocyclic or heterocyclic and is optionally substituted with a halogen, $C_1$-$C_6$ alkyl, $C_1$-$C_6$ alkoxy;

or $R^2$ has the general formula II

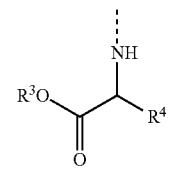

II wherein $R^1$ and $R^2$ can be identical or different;

or $R^1$ and $R^2$ have the general formula III,

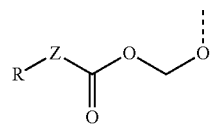

III wherein $R^1$ and $R^2$ can be identical or different;

Z is O;

R is selected from the group consisting of H, aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl;

and/or a pharmaceutical acceptable addition salt thereof and/or a stereoisomer thereof and/or a solvate thereof.

2. The compound according to statement 1, wherein B is selected from the group of adenine, thymine, cytosine and guanine.

3. The compound according to statement 1 or 2, wherein $R^2$ is O-Ph

4. The compound according to any one of statements 1 to 3, wherein $R^3$ is selected from $C_1$-$C_{10}$ alkyl.

5. The compound according to any one of statements 1 to 4, wherein X is $C_1$-$C_{10}$ alkyl and $R^5$ is $C_1$-$C_{10}$ alkyl.

6. The compound according to any of statements 1 to 5, wherein $R^2$ is O-Ph, and wherein $R^1$ is selected from the group consisting of

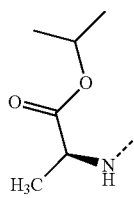

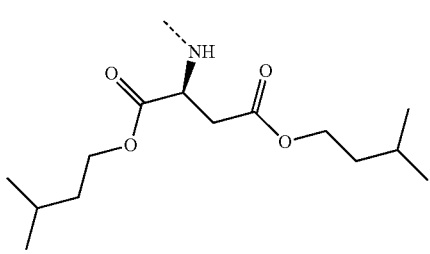

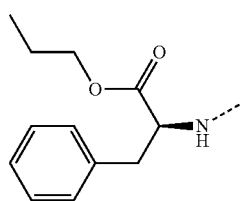

7. The compound according to statement 1 or 2, wherein $R^1$ and $R^2$ are identical and are selected from the group consisting of:

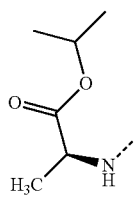

-continued

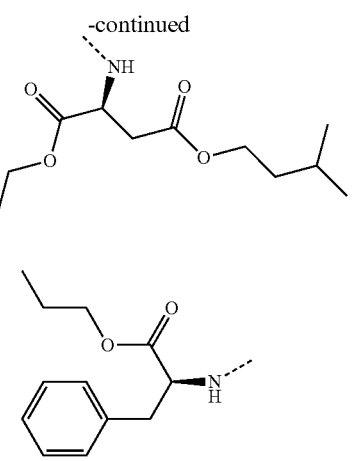

8. A compound selected from the group consisting of:
1'α-(Adenin-9-yl)-2'-deoxy-3'-O—{[N,N'-bis(n-propyl-L-phenylalaninate)]methylphosphonobisamidate}-L-threose; 1'α-(Adenin-9-yl)-2'-deoxy-3'-O—{[N-(isopropyl-L-alaninate)](phenoxy)methylphosphonoamidate]}-L-threose; 1'α-(Adenin-9-yl)-2'-deoxy-3'-O—{[N-(diisoamyl-L-aspartate)](phenoxy)methylphosphonoamidate}-L-threose; 1'α-(Thymin-1-yl)-2'-deoxy-3'-O—[N, N'-bis(n-propyl-L-phenylalaninate)) methylphosphonobisamidate]-L-threose; 1'α-(Thymin-1-yl)-2'-deoxy-3'-O—{[N-(isopropyl-L-alaninate)](phenoxy)methylphosphonoamidate}-L-threose; 1'α-(Thymin-1-yl)-2'-deoxy-3'-{[N-(diisoamyl-L-aspartate)](phenoxy)methylphosphonoamidate}-L-threose; 1'α-(Cytosin-1-yl)-2'-deoxy-3'-O—{[N, N-bis(n-propyl-L-alaninate)]methylphosphonobisamidate}-L-threose; 1'α-(Cytosin-1-yl)-2'-deoxy-3'-O—{[N-(isopropyl-L-alaninate)](phenoxy)methylphosphonoamidate}-L-threose; 1'α-(Guanin-9-yl)-2'-deoxy-3'-O—[N,N'-bis(n-propyl-L-phenylalaninate)]methylphosphonobisamidate]-L-threose; 1'α-(Guanin-9-yl)-2'-deoxy-3'-O—[N,N'-bis(n-propyl-L-alaninate)]methylphosphonobisamidate]-L-threose; and 1'α-(Guanin-9-yl)-2'-deoxy-3'-O—{[N-(isopropyl-L-alaninate)](phenoxy)methylphosphonoamidate}-L-threose, with respectively the following structural formula's:

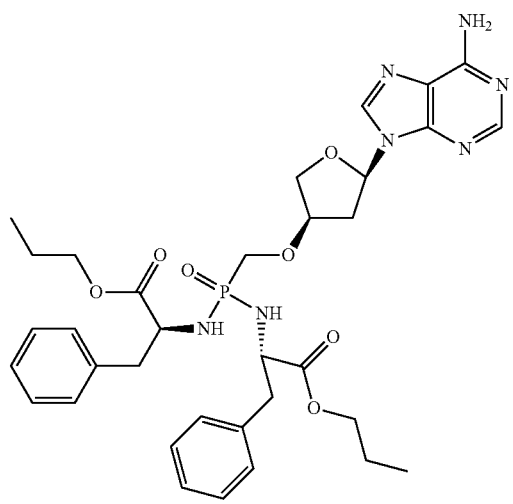

7
-continued
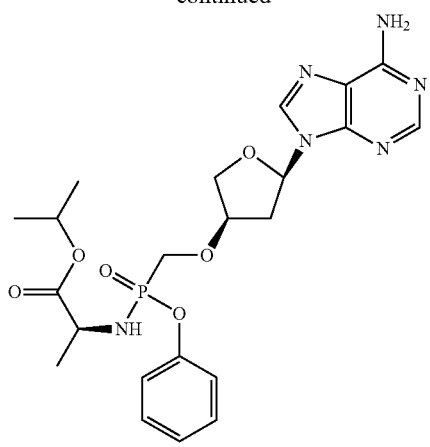
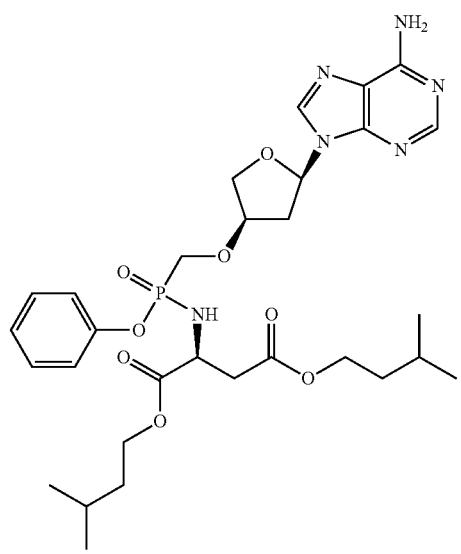
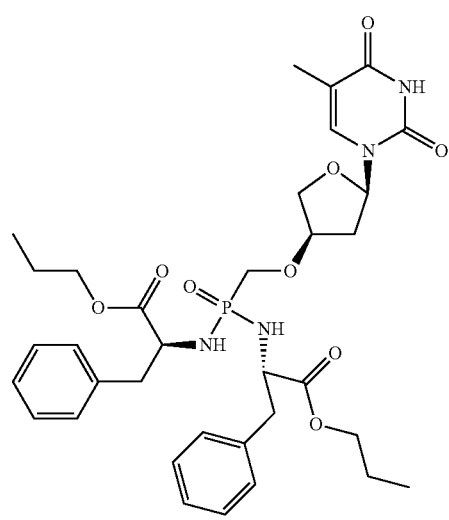
8
-continued
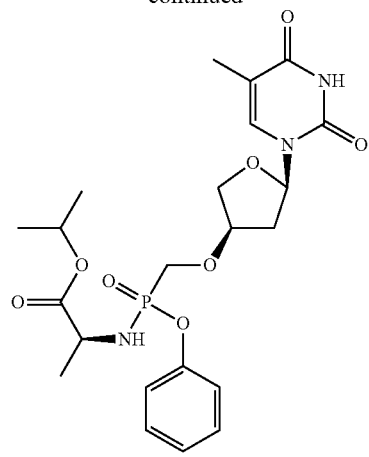
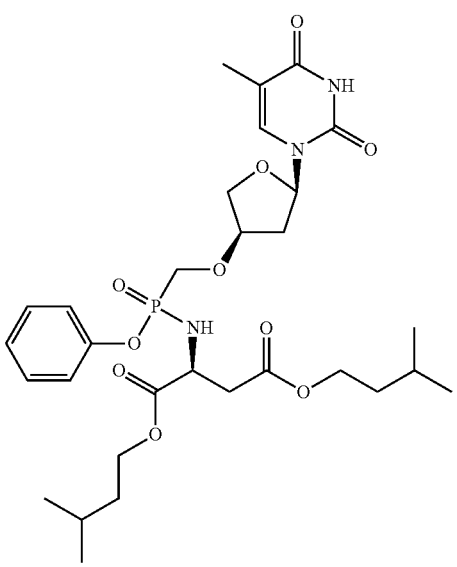
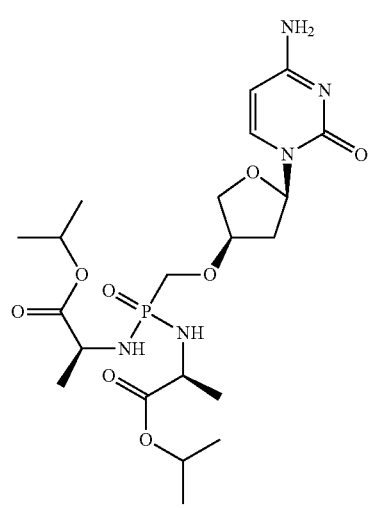

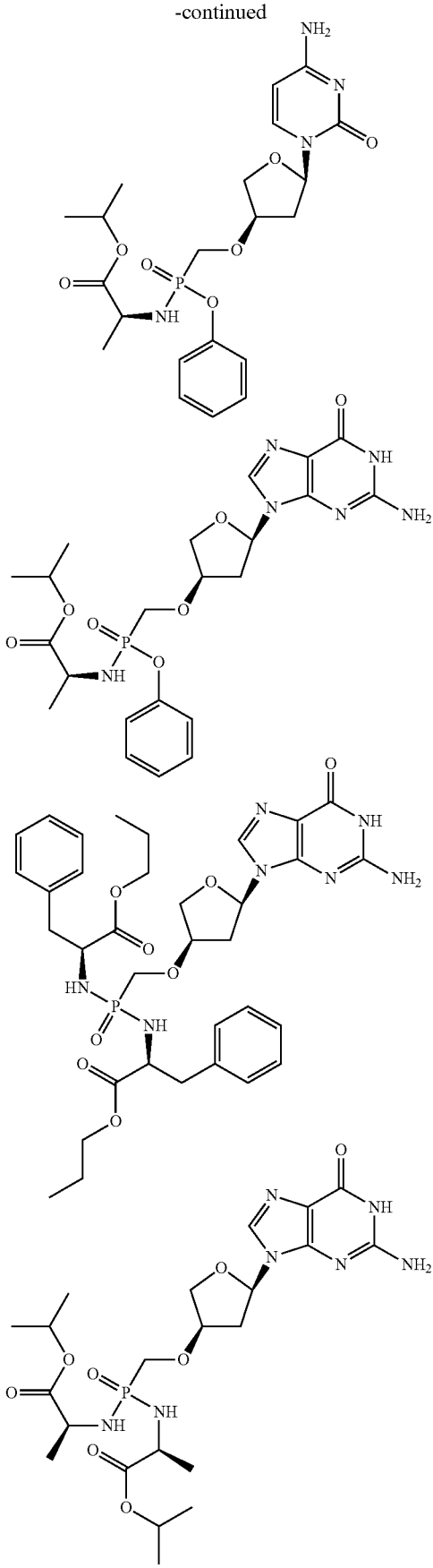

9. A compound according to any one of statements 1 to 8 for use as a medicine.

10. A compound according to any one of statements 1 to 8 for use as a medicine for the prevention or treatment of a viral infection in an animal, mammal or human.

11. The compound according to statement 10, wherein said viral infection is an infection of HBV, HIV, HCV, RSV, dengue virus, influenza virus, CMV, adenovirus, parainfluenza, rhinovirus, BK virus, and/or HSV.

12. A compound according to any one of statements 1 to 8 for use as a medicine for the prevention or treatment of a proliferative disorder such as cancer in an animal, mammal or human.

13. A pharmaceutical composition comprising a therapeutically effective amount of a compound according to any one of statements 1 to 8 and one or more pharmaceutically acceptable excipients.

14. The pharmaceutical composition according to statement 13, further comprising one or more biologically active drugs being selected from the group consisting of antiviral drugs and/or antiproliferative drugs.

15. A method of prevention or treatment of a viral infection in an animal, mammal or human, comprising the administration of a therapeutically effective amount of a compound according to any of statements 1 to 8, optionally in combination with one or more pharmaceutically acceptable excipients.

16. A method of prevention or treatment of a proliferative disorder in an animal, mammal or human, comprising the administration of a therapeutically effective amount of a compound according to any of statements 1 to 8, optionally in combination with one or more pharmaceutically acceptable excipients.

17. A process for preparing a compound according to any one of statements 1 to 8, comprising reacting the corresponding nucleoside phosphonate, or a salt thereof, with an amino acid ester, or a salt thereof, and optionally a monocyclic or fused bicyclic aromatic or heteroaromatic hydroxy compound, said reaction occurring optionally in the presence of an activating system such as 2,2'-dithiodipyridine and triphenylphosphine.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

Scheme 1 schematically shows a method for making prodrugs of PMDTA (phosphonomethoxydeoxythreosyl adenine) and PMDTT (phosphonomethoxydeoxythreosyl thymine). Compound 1 was synthesized from L-Ascorbic acid following a procedure as described in the literature (Schoning, K. U.; Scholz, P.; Wu, X. L.; Guntha, S.; Delgado, G.; Krishnamurthy, R.; Eschenmoser, A. *Helv. Chim. Acta* 2002, 85, 4111; Dumbre, S. G., Jang, M., Herdewijn, P. *J. Org. Chem.* 2013, 78, 7137-7144). The 3'-hydroxyl group of compound 1 was silylated with TBSCl (88%) followed by the DIBAL-H mediated reduction of the lactone to the lactol and acetylation, affording the key intermediate 3 in 73% yield. The Vorbrüggen glycosylation of silylated benzoyl adenine and thymine using trimethylsilyl trifluoromethanesulfonate (TMSOTf) at 65° C. in acetonitrile gave compound 4 and 5 in 56% and 83% yield, respectively. The TBS group was removed by treatment with $Et_3N \cdot 3HF$ in THF, and the phosphonate function was introduced using diisopropylphosphonomethyl triflate and NaH in THF at −15° C. afforded compound 8 and 9 in 80% and 85% yield, respectively. The benzoyl group at the 3' position was removed with $NaOH/THF/H_2O$ or $LiOH/MeOH/H_2O$. 2'-deoxygenation carried out under standard Barton deoxygenation conditions gave compounds 12 and 13 in 98% and 97% yields respectively. The benzoyl group of compound 12 was removed with ammonia in methanol, and the hydrolysis of the phosphonate ester function of 13 and 14 was carried out with TMSBr or TMSI in the presence of 2,6-lutidine at room temperature to furnish the target compounds PMDTA 15 and PMDTT 16. The monoamidate and phosphonodiamidate prodrugs 17-22 of PMDTA and PMDTT were synthesized similarly to a procedure as described in the literature (Mackman, R. L., Ray, A. S., Hui, H. C., Zhang, L., Birkus, G., Boojamra C. G., Desai, M. C, Douglas, J. L., Gao, Y., Grant, D., Laflamme, G., Lin, K. Y., Markevitch, D. Y., Mishra, R., McDermott, M., Pakdaman, R., Petrakovsky, O. V., Vela, J. E., Cihlar, T. *Bioorg. Med. Chem.* 2010, 18, 3606-3617) for preparing prodrugs of the nucleoside phosphonate HIV reverse transciptase inhibitor GS-9148.

Scheme 1

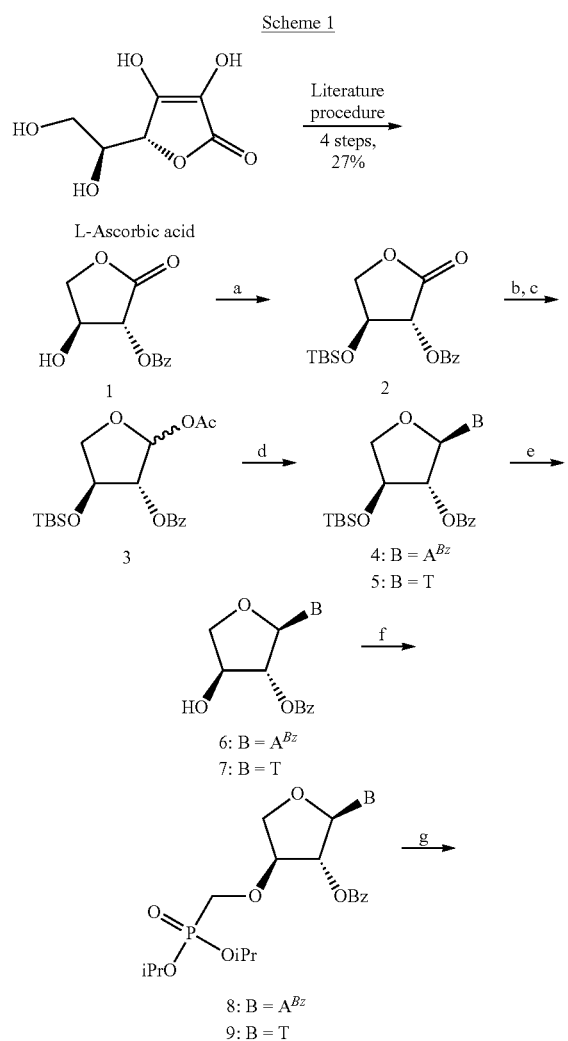

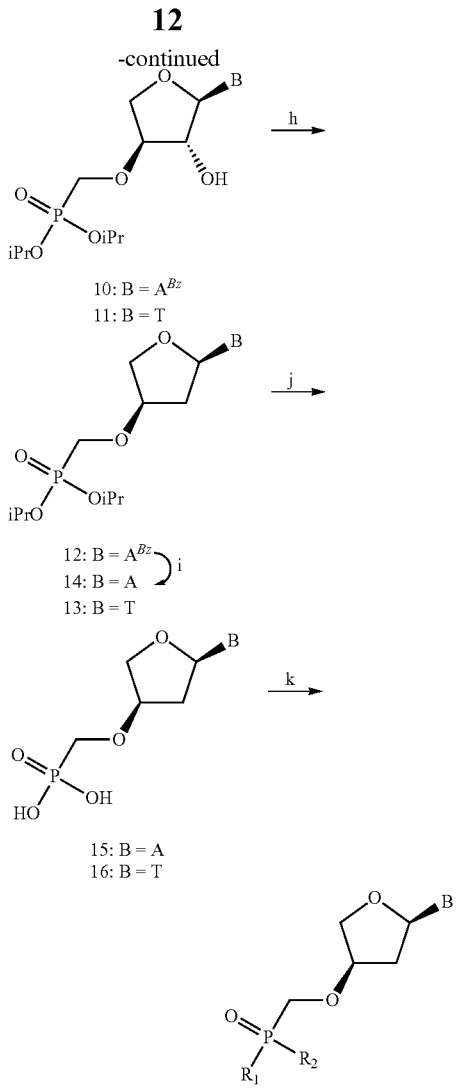

A = adenine
T = thymine
$A^{Bz}$ = N-6-benzoyladenine
Bz = benzoyl
TBS = tert-butyldimethylsilyl B = A   17: $R_1 = R_2$ = Phe-n-Pr
        18: $R_1$ = Ala-i-Pr, $R_2$ = OPh
        19: $R_1$ = Asp-i-amyl, $R_2$ = OPh
B = T   20: $R_1 = R_2$ = Phe-n-Pr
        21: $R_1$ = Ala-i-Pr, $R_2$ = OPh
        22 $R_1$ = Asp-i-amyl, $R_2$ = OPh Reagents and conditions: (a) TBSCl, cat. DMAP, Im, 0° C. to room temperature, overnight, 97%; (b) DIBAL—H, dry THF, -70 to -60° C., 3 h; (c) acetic anhydride, $Et_3N$, dry $CH_2Cl_2$, 0° C. to room temperature, overnight, 73% for 2 steps; (d) BSA, TMSOTf, MeCN, 56% for 4, 83% for 5; (e) $Et_3N \cdot 3HF$, THF, 97% for 6, 99% for 7; (f) $(^iPrO)_2POCH_2OTf$, NaH, THF, 80% for 8, 85% for 9; (g) NaOH, $THF/H_2O$, 80% for 10; LiOH, $H_2O/MeOH$, 85% for 11; (h) (1) TCD, DMAP, DCM; (2) $Bu_3SnH$, AIBN, toluene, 98% for 12, 97% for 13; (i) sat. $NH_3$ in MeOH, 92%; (j) TMSBr, 2,6-lutidine, MeCN, 60% for 15; TMSI, 2,6-lutidine, MeCN, 65% for 16; (k) amino acid esters, Aldrithiol-2, $PPh_3$, Pyridine, 34%-73%.

Scheme 2 schematically shows a method for making prodrugs of PMDTC (phosphonomethoxydeoxythreosyl cytosine). Treatment of 2b (synthesized according to a literature procedure, as described in Dumbre, S. et al. *J. Org. Chem.* 2013, 78, 7137-7144) with methanol in the presence of acetic chloride gave methyl threonoside 23 in 83% yield. The phosphonate function was introduced using diisopropylphosphonomethyl triflate and NaH in THF at −5° C. affording 3'O-phosphonomethylated 24 as the mixture of diastereoisomers in 87% yield. This methyl threonoside 24 was converted into the 1',2'-diacyl glycosyl donor 25 in 83% yield. The Vorbrüggen glycosylation of presilylated N-4-benzoylcytosine using trimethylsilyl trifluoromethanesulfonate (TMSOTf) as the Lewis acid at 0° C. in anhydrous acetonitrile, gave cytosine threonucleoside 26 in 40% yield. Its corresponding prodrugs 31 and 32 were synthesized from 26 following the protocol as described for the prodrugs of PMDTA and PDMTT in Scheme 1.

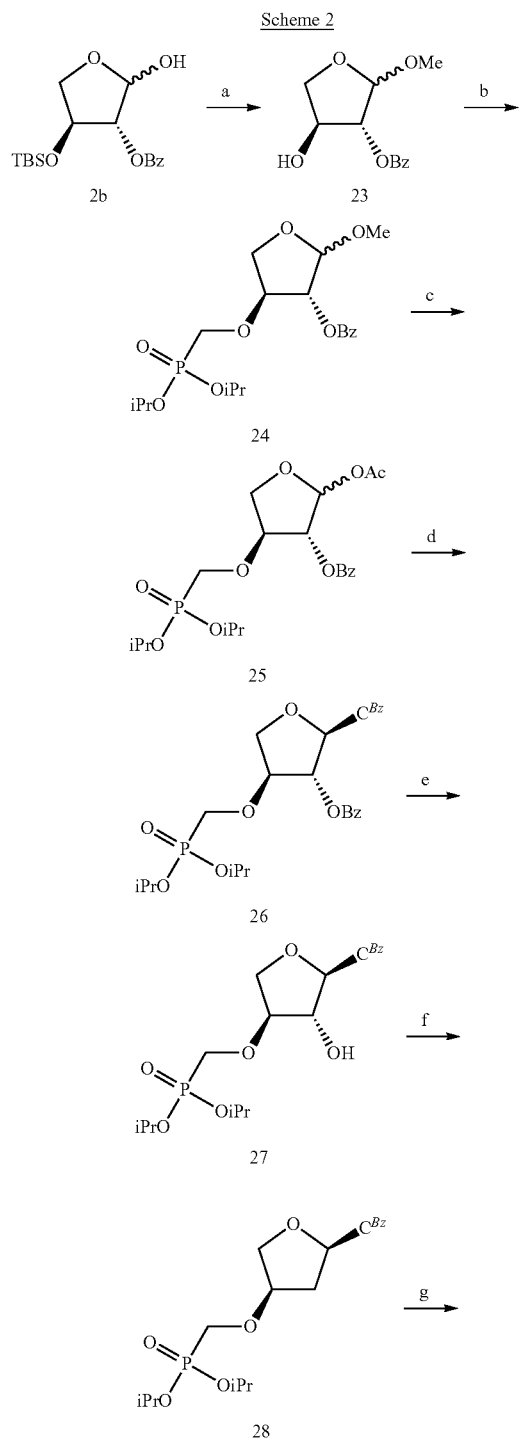

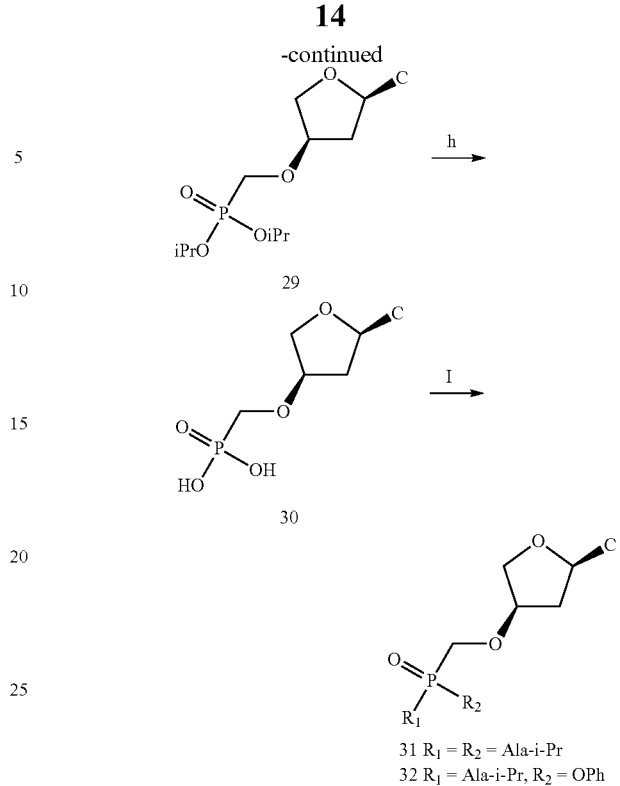

TBS = tert-butyldimethylsilyl
Bz = benzoyl
C = cytosine
$C^{Bz}$ = N-4-benzoylcytosine
Reagents and conditions: (a) AcCl, MeOH, 83%; (b) ($^{i}$PrO)$_2$POCH$_2$OTf, NaH, THF, 87%; (c) acetic anhydride, H$_2$SO$_4$, CH$_2$Cl$_2$, 83%; (d) N$^4$-benzoylcytosine, BSA, TMSOTf, MeCN, 40%; (e) NaOH, THF/MeOH/H$_2$O, 80%; (f) (1) TCDI, DMAP, DCM; (2) Bu$_3$SnH, AIBN, toluene, 70%; (g) sat. NH$_3$ in MeOH, 88%; (h) TMSI, 2,6-lutidine, MeCN, 48%; (I) amino acid esters, Aldrithiol-2, PPh$_3$, Pyridine.

The prodrugs of PMDTG (phosphonomethoxydeoxythreosyl guanosine) were synthesized as depicted in Scheme 3. The Vorbrüggen glycosylation of the threose derivative 3 with 2-amino-6-chloropurine using trimethylsilyl trifluoromethanesulfonate (TMSOTf) as the Lewis acid at 70° C. in anhydrous acetonitrile gave compound 33 in 67% yield. The TBS group was removed by treatment with Et$_3$N.3HF in THF and the phosphonate function was introduced using diisopropylphosphonomethyl triflate and NaH in THF at −5° C. to afford nucleoside 35 in 67% yield. The benzoyl group at the 2' position was hydrolyzed with 2N NH$_3$ in methanol which upon Barton's reductive 2'-deoxygenation gave the 2'-deoxy nucleoside 37 in 68% yield. After the hydrolysis of the phosphonate ester function in 37, the 6-chloro group was transformed to hydroxyl group by refluxing with 2-mecaptoethanol and NaOMe in methanol to afford PMDTG 38 in 49% yield. The prodrugs of PMDTG (39, 40 and 41) were synthesized using the same procedure as described for the prodrugs of PMDTA and PMDTT in Scheme 1.

Scheme 3

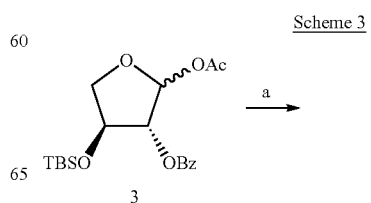

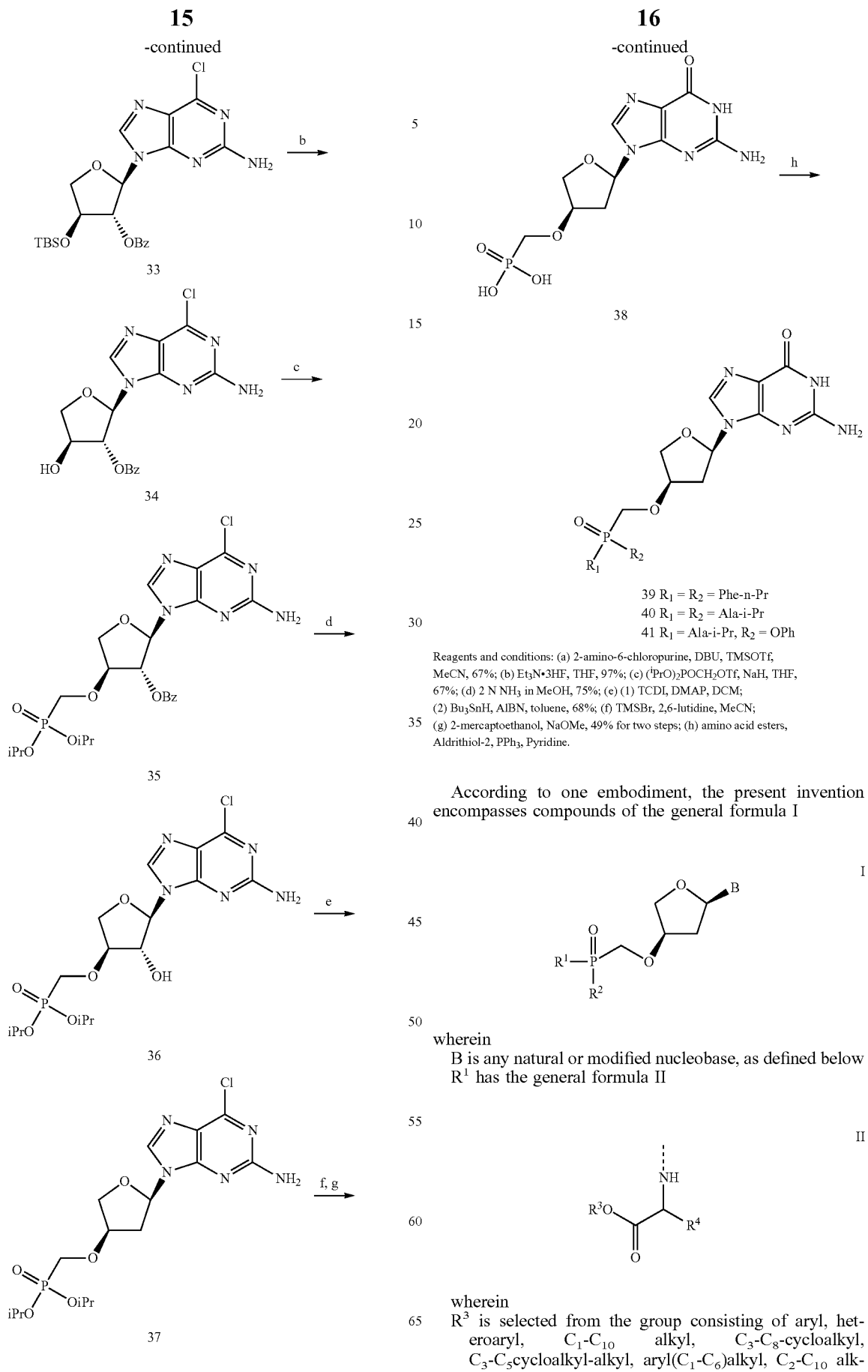

Reagents and conditions: (a) 2-amino-6-chloropurine, DBU, TMSOTf, MeCN, 67%; (b) Et$_3$N·3HF, THF, 97%; (c) (ⁱPrO)$_2$POCH$_2$OTf, NaH, THF, 67%; (d) 2 N NH$_3$ in MeOH, 75%; (e) (1) TCDI, DMAP, DCM; (2) Bu$_3$SnH, AIBN, toluene, 68%; (f) TMSBr, 2,6-lutidine, MeCN; (g) 2-mercaptoethanol, NaOMe, 49% for two steps; (h) amino acid esters, Aldrithiol-2, PPh$_3$, Pyridine.

According to one embodiment, the present invention encompasses compounds of the general formula I wherein
B is any natural or modified nucleobase, as defined below
R$^1$ has the general formula II wherein
R$^3$ is selected from the group consisting of aryl, heteroaryl, C$_1$-C$_{10}$ alkyl, C$_3$-C$_8$-cycloalkyl, C$_3$-C$_5$cycloalkyl-alkyl, aryl(C$_1$-C$_6$)alkyl, C$_2$-C$_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

$R^4$ is selected from the group consisting of aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl, X—COOR$^5$, X—O(C=O)—R$^5$;

wherein X is aryl, heteroaryl, $C_1$-$C_{10}$ alkyl, $C_2$-$C_{10}$ alkenyl, $C_2$-$C_{10}$ alkynyl, $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, halo-alkyl, cyano, $C_1$-$C_7$ alkoxy;

wherein $R^5$ is selected from the group consisting of aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

$R^2$ is O—Ar, wherein Ar is a fused bicyclic aryl moiety or a monocyclic aryl moiety, either of which aryl moieties is carbocyclic or heterocyclic and is optionally substituted with a halogen, $C_1$-$C_6$ alkyl, $C_1$-$C_6$ alkoxy;

or $R^2$ has the general formula II,

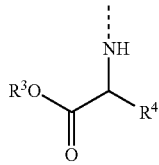

II wherein $R^1$ and $R^2$ can be identical or different;
or $R^1$ and $R^2$ have the general formula III,

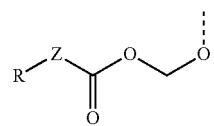

III wherein $R^1$ and $R^2$ can be identical or different;
Z is O;
R is selected from the group consisting of H, aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl;
and/or a pharmaceutical acceptable addition salt thereof and/or a stereoisomer thereof and/or a solvate thereof.

Said base (B) is selected from the group of the pyrimidine and purine bases. Such bases include natural bases, such as adenine, thymine, cytosine, uracyl, guanine and modified bases or modifications of said natural bases. In certain embodiments of the present invention said base is a guanine, cytosine, adenine, thymine, cytosine, or uracyl. In a more specific embodiment of the present invention, said base is a cytosine or uracyl. In another specific embodiment of the present invention said base is a uracyl. In another specific embodiment of the present invention said base is a thymine. In another specific embodiment of the present invention said base is an adenine. In another specific embodiment of the present invention said base is a guanine.

In another embodiment, the present invention concerns a compound according to the invention, including the compound of formula I, wherein Ar is a fused bicyclic aryl moiety or a monocyclic aryl moiety, either of which aryl moieties is carbocyclic or heterocyclic and is optionally substituted with a halogen, $C_1$-$C_6$ alkyl, $C_1$-$C_6$ alkoxy. In a more specific embodiment said Ar is phenyl. In a specific embodiment of the present invention, the compound of formula I can have any value for $R^1$ and $R^2$ as described herein, wherein Ar is phenyl.

In a more specific embodiment said $R^3$ is $C_1$-$C_{10}$ alkyl. In another specific embodiment said $R^3$ is $C_3$-$C_{10}$ alkyl. In another specific embodiment said $R^3$ is $C_1$-$C_5$ alkyl. In yet another specific embodiment said $R^3$ is $C_3$-$C_5$ alkyl.

In another specific embodiment, said $R^4$ is selected from the group consisting of $C_1$-$C_{10}$ alkyl or X—COOR$^5$, wherein $R^5$ can have any values as described herein. In a more specific embodiment, said $R^5$ is selected from the group consisting of aryl, heteroaryl, $C_1$-$C_{10}$ alkyl, $C_3$-$C_8$-cycloalkyl, $C_3$-$C_5$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl. In a more specific embodiment $R^5$ is $C_1$-$C_7$ alkyl or $C_3$-$C_8$ cycloalkyl; in a more specific embodiment $R^5$ is $C_1$-$C_5$ alkyl, and in another more specific embodiment $R^5$ is $C_3$-$C_7$ alkyl, in an even more specific embodiment $R^5$ is $C_3$-$C_5$ alkyl. In a yet more specific embodiment $R^5$ is $C_5$ alkyl. In another specific embodiment, $R^5$ is aryl-($C_1$-$C_2$)alkyl; in another more specific embodiment, $R^5$ is benzyl or phenyl-methyl.

In another specific embodiment, X is selected from the group consisting of aryl, heteroaryl, $C_1$-$C_{10}$ alkyl, $C_2$-$C_{10}$ alkenyl, $C_2$-$C_{10}$ alkynyl or $C_3$-$C_8$-cycloalkyl, and wherein said aryl, heteroaryl, $C_1$-$C_{10}$ alkyl, and $C_3$-$C_8$-cycloalkyl optionally contains one or more functions, atoms or radicals independently selected from the group consisting of halogen, carbonyl, thiocarbonyl, hydroxyl, thiol, ether, thioether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_3$-$C_{10}$ cycloalkyl, hydroxylamino, mercaptoamino, alkyl-amino, cycloalkylamino, alkenylamino, cycloalkenylamino, alkynylamino, arylamino, arylalkylamino, hydroxyalkylamino, mercaptoalkylamino, heterocyclic-substituted alkylamino, hetero-cyclic amino, heterocyclic-substituted arylamino, hydrazine, alkylhydrazino, phenylhydrazino, sulfonyl, sulfinyl and sulfonamide. In a more specific embodiment, X is selected from the group consisting of aryl, heteroaryl, $C_1$-$C_{10}$ alkyl, or $C_3$-$C_8$-cycloalkyl, more specifically said X is a $C_1$-$C_6$ alkyl, even more specifically said X is a $C_1$-$C_3$ alkyl or $C_1$-$C_2$ alkyl or —CH$_2$—.

Special novel compounds in accordance with the present invention include each of the compounds whose preparation is described in the accompanying Examples, and pharmaceutically acceptable salts and solvates thereof.

The present invention also relates to a process for preparing a compound represented by the structural formula I, or any subgroup thereof, including a final step as illustrated in step (k) of Scheme 1, step (I) of Scheme 2, or step (h) of Scheme 3. Said final step comprises reacting the corresponding nucleoside phosphonate (represented by the structural formula shown for compounds 15, 16, 30, and 38), or a salt thereof, with an amino acid ester represented by the structural formula

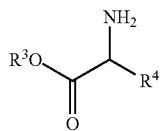

wherein $R^3$ and $R^4$ are as defined herein-above, or a salt thereof, and optionally a monocyclic or fused bicyclic aromatic or heteroaromatic hydroxy compound represented by the structural formula HO—Ar (wherein Ar is as defined herein-above), for instance a phenol or a substituted phenol. Said final reaction step occurs optionally, but preferably, in the presence of an activating system for activating the phosphonate moiety. The activating system may be such as, but not limited to, an activating combination of 2,2'-dithiodipyridine and triphenylphosphine. Said final reaction step occurs preferably in a reaction solvent such as, but not limited to, and preferably under an inert atmosphere (such as, but not limited to, nitrogen gas), within a temperature range from about 40° C. to about 80° C., depending upon the boiling temperature of the reaction solvent, and for a period of time sufficient for substantially converting all phosphonate groups.

The present invention also concerns a compound having formula I, any subgroup thereof, or stereoisomeric forms thereof, for use as a medicine.

The present invention also concerns a compound having formula I any subgroup thereof, or stereoisomeric forms thereof, for use as a medicine for the prevention or treatment of viral disorders and oncological disorders in an animal, preferably in a mammal. In an embodiment, said disorder is a viral disorder, including a disease caused by a viral infection, for example an infection with HBV, HIV, HCV, RSV, dengue virus, influenza virus, CMV, adenovirus, parainfluenza, rhinovirus, BK virus, and/or HSV; in another embodiment said disorder is an oncological disorder, which may be acute or chronic, including a proliferative disorder, especially cancer. In an embodiment, said mammal is a human being.

The present invention also concerns the use of the compounds of formula I, any subgroup thereof, or stereoisomeric forms thereof, for the manufacture of a medicament for the prevention or treatment of a viral disorder and/or an oncological disorder in an animal. In an embodiment, said animal is a mammal, preferably said mammal is a human being.

The present invention also concerns a pharmaceutical composition comprising a therapeutically effective amount of a compound having formula I, any subgroup thereof, or stereoisomeric forms thereof and one or more pharmaceutically acceptable excipients. Said composition may further comprise one or more biologically active drugs being selected from the group consisting of antiviral drugs, and antineoplastic drugs.

The present invention also concerns a method of prevention or treatment of a viral disorder in an animal, comprising the administration of a therapeutically effective amount of a compound having formula I, any subgroup thereof, or stereoisomeric forms thereof, optionally in combination with one or more pharmaceutically acceptable excipients.

The present invention also concerns a method of prevention or treatment of an oncological disorder in an animal, comprising the administration of a therapeutically effective amount of a compound having formula I, any subgroup thereof, or stereoisomeric forms thereof, optionally in combination with one or more pharmaceutically acceptable excipients.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The compounds in accordance with the present invention are beneficial in the treatment and/or prevention of various animal, mammal or human ailments or diseases. These include viral diseases, such as diseases caused by a viral infection, for example an infection with HBV, HIV, HCV, RSV, dengue virus, influenza virus, CMV, adenovirus, parainfluenza, rhinovirus, BK virus, and/or HSV; and oncological disorders such as proliferative disorders (eg. cancer).

Viral diseases include infections caused by various families of virus, including the Hepadnaviridae, Retroviridae, Flaviviridae, Picornaviridae. Various genera within the Hepadnaviridae include the Orthohepadnavirus and the Avihepadnavirus; Members of the Orthohepadnavirus genus include Hepatitis B virus (HBV) and the Woodchuck hepatitis virus. Members of the Avihepadnavirus genus include the Duck hepatitis B virus. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Flaviviridae family include Flavivirus, Pestivirus, Hepacivirus and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

The quantity of a compound of use in the invention required for the prophylaxis or treatment of a particular condition or disease will vary depending on the compound chosen and the condition of the animal, mammal or human patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

Definitions

The term "pyrimidine and purine bases" as used herein includes, but is not limited to, adenine, thymine, cytosine, uracyl, guanine and 2,6-diaminopurine and analogues thereof. A purine or pyrimidine base as used herein includes a purine or pyrimidine base found in naturally occurring nucleosides as mentioned above. An analogue thereof is a base which mimics such naturally occurring bases in such a way that their structures (the kinds of atoms and their arrangement) are similar to the naturally occurring bases but may either possess additional or lack certain of the functional properties of the naturally occurring bases. Such analogues include those derived by replacement of a CH moiety by a nitrogen atom (e.g. 5-azapyrimidines such as 5-azacytosine) or vice versa (e.g. 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g. halogen, hydroxyl, amino, ($C_1$-$C_6$) alkyl and others. Such purine or pyrimidine bases, and analogues thereof, are well known to those skilled in the art, e.g. as shown at pages 20-38 of WO 03/093290.

In particular purine and pyrimidine analogues B for the purpose of the present invention may be selected from the group comprising pyrimidine bases represented by the structural formula (IV):

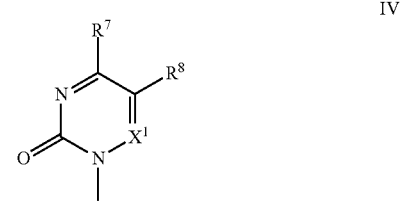

IV and purine bases represented by the structural formula (V):

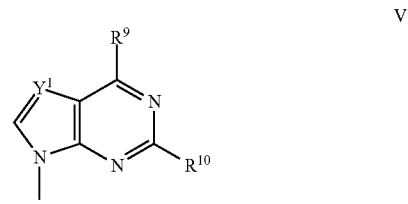

V wherein:
$R^7$ and $R^9$ are independently selected from the group consisting of H, —OH, —SH, —$NH_2$, and —NH-Me;
$R^8$ and $R^{10}$ are independently selected from the group consisting of H, methyl, ethyl, isopropyl, hydroxyl, amino, ethylamino, trifluoromethyl, cyano and halogen; and
$X^1$ and $Y^1$ are independently selected from CH and N.

Just as a few non-limiting examples of pyrimidine analogues, can be named substituted uracils with the formula (IV) wherein $X^1$ is CH, $R^7$ is hydroxyl, and $R^8$ is selected from the group consisting of methyl, ethyl, isopropyl, amino, ethylamino, trifluoromethyl, cyano, fluoro, chloro, bromo and iodo.

The term "alkyl" as used herein refers to a straight (normal) or branched (eg. secondary, or tertiary) hydrocarbon chains having the number of carbon atoms as indicated (or where not indicated, preferably having 1-20, more preferably 1-6 carbon atoms). The term "$C_1$-$C_6$ alkyl" refers to such hydrocarbon chains having from 1 to 6 carbon atoms. Examples thereof are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl.

As used herein and unless otherwise stated, the term "cycloalkyl" means a monocyclic saturated hydrocarbon monovalent radical having the number of carbon atoms as indicated (or where not indicated, preferably having 3-20, more preferably 3-10 carbon atoms, more preferably 3-8 or 3-6 carbon atoms). "$C_3$-$C_8$ cycloalkyl" refers to such monocyclic saturated hydrocarbon monovalent radical having from 3 to 8 carbon atoms, such as for instance cyclopropyl, cyclobutyl, cyclopentyl, cyclohexyl, cycloheptyl, cyclooctyl.

The term "alkoxy" refers to the group alkyl-O—, where alkyl is as defined above. "($C_1$-$C_6$) alkoxy" as used herein includes but is not limited to methoxy, ethoxy, propoxy, isopropoxy, butoxy, iso-butoxy, sec-butoxy, pentoxy, 3-pentoxy, or hexyloxy.

As used herein and unless otherwise stated, the term "halogen" or "halo" means any atom selected from the group consisting of fluorine (F), chlorine (Cl), bromine (Br) and iodine (I).

As used herein and unless otherwise stated, the term "Ar" or "aryl" means a monovalent unsaturated aromatic carbocyclic radical having one, two, three, four, five or six rings, preferably one, two or three rings, which may be fused or bicyclic. An aryl group may optionally be substituted by one, two, three or more substituents as set out in this invention with respect to optional substituents that may be present on the group Ar or aryl. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. Preferred substituent groups of Ar are independently selected from halogen, $C_1$-$C_6$ alkyl, $C_1$-$C_6$ alkoxy, hydroxy (—OH), acyl (R'—C(=O)—), acyloxy (R'—C(=O)—O—), nitro (—NO$_2$), amino (—NH$_2$), —SO$_3$H, —SH, —SR', wherein R' is an alkyl. Preferred Ar are phenyl, bromophenyl and naphthyl.

EXAMPLES

Experimental Section

NMR spectra were recorded on a Bruker Advance 300 ($^1$H NMR, 300 MHz; $^{13}$C NMR, 75 MHz; $^{31}$P NMR, 121 MHz) or 500 MHz ($^1$H NMR, 500 MHz; $^{13}$C NMR, 125 MHz) or 600 MHz ($^1$H NMR, 600 MHz; $^{13}$C NMR, 150 MHz) spectrometers with tetramethylsilane (TMS) as internal standard or referenced to the residual solvent signal. Two dimensional NMRs (H—COSY, NOESY, HSQC, and HMBC) were used for the assignment of the intermediates and final compounds. The mass spectra were measured on a quadrupole orthogonal acceleration time-of-flight mass spectrometer. Preparative HPLC purifications were performed on columns packed with 10 um $C_{18}$ reverse-phase resin, 21×250 mm. Column chromatography was performed on silica gel (100-200 mesh or 230-400 mesh). The solvents for the reactions were distilled prior to use (THF and toluene from Na/benzophenone; CH$_2$Cl$_2$ and CH$_3$CN from CaH$_2$; Et$_3$N from KOH).

Example 1: Synthesis of Calcium-L-threonate Monohydrate (1a)

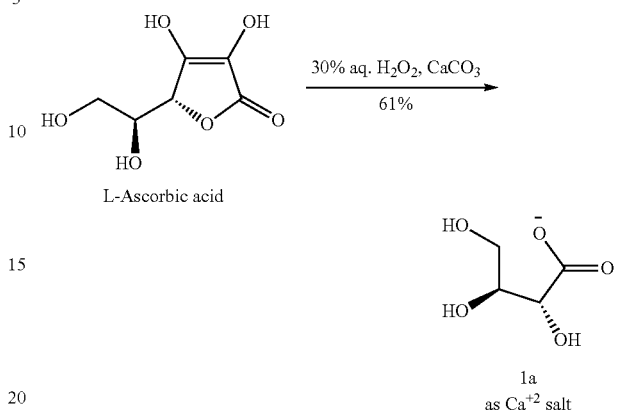

This compound was synthesized according to a known procedure (Schoning, K. U.; Scholz, P.; Wu, X. L.; Guntha, S.; Delgado, G.; Krishnamurthy, R.; Eschenmoser, A. *Helv. Chim. Acta* 2002, 85, 4111).

To a solution of 200 g (1.14 mol) of L-ascorbic acid dissolved in 1.6 L of distilled water, 227 g (2.27 mol) of CaCO$_3$ was slowly added with stirring, and the slurry was cooled 20 to 15° C. To this mixture, 455 ml of 30% aq. H$_2$O$_2$ solution was added, at 12-18° C., over a period of 6 hours, and the mixture was stirred at room temperature for 18 hours. The mixture, under constant stirring, was treated with 45 g of charcoal and heated to 70° C., stirred for 3 hours. The hot suspension was filtered, and the solid washed with 2×38 ml of distilled water. The washings were combined with the filtrate and concentrated to 1.52 L under reduced pressure. The resulting solution was stirred, and 455 ml of MeOH was slowly added over a period of 5 hours. After stirring for 5 hours, another 455 ml of MeOH was slowly added. The solids were isolated by filtration, washed with 2×100 ml of MeOH, and dried under reduced pressure to constant weight. The combined filtrates were concentrated, MeOH was slowly added, and the resulting precipitate was isolated by filtration. The procedure was repeated, and the first two crops gave 107.8 g (61%) of 1a as a colourless powder.

Example 2: 2-O-Benzoyl-L-threonolactone (1)

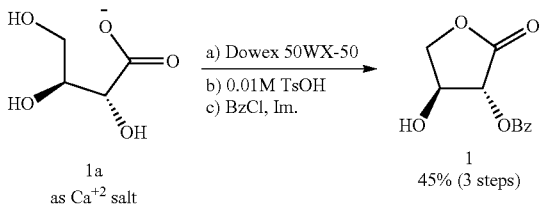

This compound was made according to a known procedure (Schoning, K. U.; Scholz, P.; Wu, X. L.; Guntha, S.; Delgado, G.; Krishnamurthy, R.; Eschenmoser, A. *Helv. Chim. Acta* 2002, 85, 4111; and Dumbre, S. G., Jang, M., Herdewijn, P. *J. Org. Chem.* 2013, 78, 7137-7144).

To a solution of 27 g (143 mmol) of 1a in 570 mL of warm H$_2$O, 400 ml of Dowex 50WX4-50 resin was added, and the mixture was vigorously stirred at 70° C. stirred for 30 min. The resin was removed by filtration and washed with H₂O (50 mL×2). The washings were combined with the filtrate and evaporated to dryness under reduced pressure. The residue was co-evaporated with MeCN (200 mL×3). The residue was then suspended in 285 ml of dry MeCN, and 0.57 g (3.32 mmol) of TsOH was added. The mixture was refluxed for 23 hours, cooled, filtered, and the solvent was removed under reduced pressure. The residue was dissolved in dry acetonitrile, imidazole (24.48 g, 360 mmol) was added and benzoyl chloride (18.99 mL, 163 mmol) was slowly added over a period of 10 minutes at 0 to −5° C., The reaction mixture was stirred at room temperature overnight. Acetonitrile was removed under reduced pressure, the residue was taken up into 300 mL of EtOAc, and 200 mL of water was added. The resulting mixture was sequentially washed with 2×150 mL of ice-cold 1 M HCl soln., 150 mL of water, 150 mL of sat. NaHCO₃ soln., and 200 mL of sat. aq. NaCl soln. The organic layer was dried over anhydrous NaSO₄ and concentrated. The residue was purified by column chromatography (2:1 to 1:2, hexane/EtOAc) to obtain 1 (16.5 g, 45% yield) as white solid.

$^1$H NMR (300 MHz, DMSO): δ 8.05 (d, J=7.7 Hz, 2H, Ph), 7.73 (t, J=8.1 Hz, 1H, Ph), 7.58 (t, J=7.7 Hz, 2H, Ph), 6.15 (d, J=5.0 Hz, 1H, 3'-OH), 5.74 (d, J=7.8 Hz, 1H, H2'), 4.71-4.80 (m, 1H, H3'), 4.56 (t, J=8.1 Hz, 1H, H4a'), 4.10 (t, J=8.1 Hz, 1H, H4b');

$^{13}$C NMR (75 MHz, DMSO): δ 171.2 (C-1), 164.9 (Bz-CO), (134.2, 129.7, 129.1, 128.6) (Ph), 75.2 (C-2'), 69.8 (C-3' and C-4').

Example 3: Synthesis of (Hydroxymethyl)diisopropylphosphonate

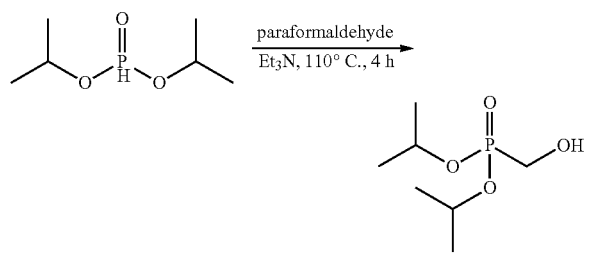

This compound was synthesized according to a known procedure (Kiyokawa, K.; Suzuki, I.; Yasuda, M.; Baba, A. *Eur. J. Org. Chem.* 2011, 2163.

To a mixture of diisopropyl phosphite (50 g, 301 mmol) and paraformaldehyde (12.2 g, 391 mmol) was added triethylamine (4.82 mL, 34.6 mmol). The mixture was heated to 110° C. for 4 hours. The solution was diluted with 500 ml of EtOAc and washed with brine, dried over anhydrous Na₂SO₄ and concentrated to give the product (53 g, 90%) as a colourless oil.

$^1$H NMR (300 MHz, CDCl₃): δ 4.68-4.79 (m, 2H, CH(CH₃)₂), 4.61 (d, J=3.9 Hz, OH), 3.84 (t, $^1J_{P,H}$=6.1 Hz, 2H, PCH₂), 1.32-1.35 [m, 12H, CH(CH₃)₂];

$^{13}$C NMR (75 MHz, CDCl₃): δ 71.1 [CH(CH₃)₂, $^2J_{P,C}$=7.0 Hz], 57.5 (PCH₂, $^2J_{P,C}$=163.3 Hz), 23.9 [CH(CH₃)₂].

$^{31}$P NMR (121 MHz, CDCl₃): δ 22.7

Example 4: Synthesis of Diisopropylphosphonomethyl Trifluoromethanesulfonate

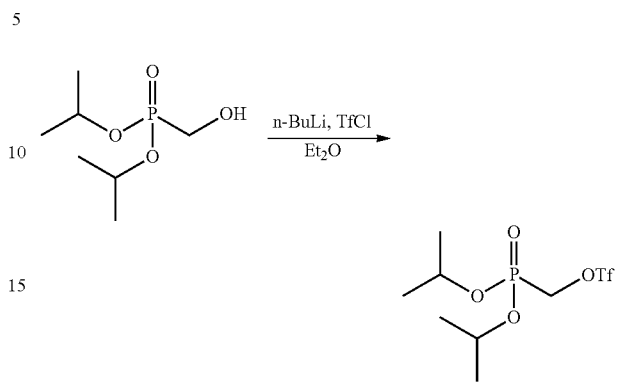

This compound was synthesized according to a known procedure: Dumbre, S. G., Jang, M., Herdewijn, P. *J. Org. Chem.* 2013, 78, 7137-7144.

To a solution of (hydroxymethyl)diisopropylphosphonate (10.0 g, 50.97 mmol) in 170 mL of dry diethyl ether at −78° C. was added a solution of 1.6 M n-BuLi (35.04 mL, 56.07 mmol). The reaction mixture was allowed to stir at this temperature for 5 min and trifluoromethanesulfonyl chloride (5.97 mL, 56.07 mmol) was added dropwise over 5 minutes. The reaction mixture was stirred at this temperature for 1 h. and was quenched with sat. NH₄Cl. The organic layer was washed with brine, dried over NaSO₄, and concentrated under reduced pressure at rt gave diisopropylphosphonomethyl triflate (16.1 g, 96% yield).

$^1$H NMR (300 MHz, CDCl₃): δ 4.77-4.88 [m, 2H, CH(CH₃)₂], 4.56 (d, $^1J_{P,H}$=8.98 Hz, 2H, PCH₂), 1.36-1.40 [m, 12H, CH(CH₃)₂];

$^{13}$C NMR (75 MHz, CDCl₃): δ 118.4 (d, $^1J_{C,F}$=318.8 Hz, CF₃), 73.0 [d, $^2J_{P,C}$=6.7 Hz, CH(CH₃)₂], 67.0 (d, $^2J_{P,C}$=169.8 Hz, PCH₂), 23.7 [CH(CH₃)₂].

$^{31}$P NMR (121 MHz, CDCl₃): δ 10.0

Example 5: Synthesis of 2-O-Benzoyl-3-O-tert-butyldimethylsilyl-L-threonolactone (2)

This compound was synthesized according to a known procedure: Dumbre, S. G., Jang, M., Herdewijn, P. *J. Org. Chem.* 2013, 78, 7137-7144; and Vina, D.; Wu, T. F.; Renders, M.; Laflamme, G.; Herdewijn, P. *Tetrahedron* 2007, 63, 2634.

To a solution of lactone (29.8 g, 134 mmol), cat. DMAP (0.1 g), and imidazole (15.75 g, 231 mmol) in dry acetonitrile at 0° C., a solution of tert-butyldimethylchlorosilane (22.24 g, 148 mmol) in dry acetonitrile was added dropwise. The reaction mixture was allowed to warm to room temperature and stirred overnight. The acetonitrile was removed under reduced pressure, the residue was taken up into 500 mL of ethyl ether, and 300 mL of water was added. The resulting mixture was sequentially washed with ice cold 1 M HCl soln., water, sat. NaHCO₃ soln., and sat. aq. NaCl soln. The organic layer was dried over Na₂SO₄ and concentrated. The residue was purified by column chromatography (hexane/EtOAc=4:1) to afford 2 (44 g, 97% yield) as a colourless oil.

$^1$H NMR (300 MHz, CDCl₃): δ 8.06-8.09 (m, 2H, Bz-H), 7.58-7.63 (m, 2H, Bz-H), 7.44-7.49 (m, 2H, Bz-H), 5.59 (d, J=7.3 Hz, 1H, H2'), 4.80 (q, J=7.2 Hz, 1H, H3'), 4.53 (dd,

J=9.1, 7.0 Hz, 1H, H4a'), 4.09 (dd, J=9.1, 7.3 Hz, 1H, H4b'), 0.86 [s, 9H, C(CH$_3$)$_3$], 0.07 (s, 3H, SiCH$_3$), 0.06 (s, 3H, SiCH$_3$);

$^{13}$C NMR (75 MHz, CDCl$_3$): δ 170.4 (C-1), 165.2 (Bz-CO), [133.9, 130.1, 128.7 (Ph)], 75.1 (C-2), 71.7 (C-3), 70.6 (C-4), 25.6 [C(CH$_3$)$_3$], 18.0 [C(CH$_3$)$_3$], −4.7 (SiCH$_3$), −4.9 (SiCH$_3$); HRMS: [M+H]$^+$ calculated for C$_{17}$H$_{25}$O$_5$Si, 337.1466; found, 337.1460.

Example 6: Synthesis of 1-O-Acetyl-2-O-benzoyl-3-O-tert-butyldimethylsilyl-$_L$-threofuranose (3)

This compound was synthesized from compound 2 as described in the literature (Vina, D.; Wu, T. F.; Renders, M.; Laflamme, G.; Herdewijn, P. *Tetrahedron* 2007, 63, 2634). α isomer: $^1$H NMR (300 MHz, CDCl$_3$): δ 8.02-8.05 (m, 2H, Bz-H), 7.54-7.60 (m, 2H, Bz-H), 7.41-7.46 (m, 2H, Bz-H), 6.49 (d, J=4.4 Hz, 1H, H1'), 5.26 (t, J=4.7 Hz, 1H, H2'), 4.68-4.73 (m, 1H, H3'), 4.27 (dd, J=9.1, 6.5 Hz, 1H, H4a'), 3.78 (dd, J=9.0, 4.7 Hz, 1H, H4b'), 1.94 (s, 3H, CH$_3$CO), 0.87 (s, 9H, C(CH$_3$)$_3$), 0.09 (s, 3H, SiCH$_3$), 0.08 (s, 3H, SiCH$_3$);

$^{13}$C NMR (75 MHz, CDCl$_3$): δ 169.4 (CH$_3$CO), 165.4 (Bz-CO), [133.4, 129.7, 129.2, 128.5 (Ph)], 94.65 (C-1'), 80.0 (C-2'), 73.4 (C-3'), 72.5 (C-4'), 25.6 [C(CH$_3$)$_3$], 20.9 (CH$_3$CO), 17.9 [C(CH$_3$)$_3$], −4.7 (SiCH$_3$), −5.0 (SiCH$_3$); HRMS: [M+Na]$^+$ calculated for C$_{19}$H$_{28}$O$_6$SiNa, 403.1548; found, 403.1548.

Example 7: Synthesis of 1'α-(N$^6$—Benzoyladenin-9-yl)-2'-O-benzoyl-3'-O-tert-butyldimethylsilyl-L-threose (4)

A suspension of compound 3 (0.51 g, 1.35 mmol) and dry N$^6$-benzoyladenine (0.355 g, 1.49 mmol) in 15 ml of abs. MeCN was treated with 0.73 ml (3.0 mmol) of BSA and heated to 65° C. Stirring and heating was continued until a clear soln. was formed (ca. 1 h) and 0.49 ml (2.7 mmol) of TMSOTf was added. After heating at 65° C. for 16 hours, the mixture was cooled to rt and poured into an ice-cold 100 ml of sat. aq. NaHCO$_3$ soln./AcOEt 1:1. The org. layer was separated, the aq. layer was extracted with AcOEt, and the combined org. layers were washed with brine and dried over Na$_2$SO$_4$. Evaporation of the solvent and column chromatography (5:2 CH$_2$Cl$_2$/AcOEt) gave 4 (0.42 g, 56% yield) as white foam.

$^1$H NMR (300 MHz, CDCl$_3$): δ 9.60 (s, 1H, NH), 8.67 (s, 1H, H2), 8.37 (s, 1H, H8), 7.94-8.00 (m, 4H, Bz-H), 7.47-7.55 (m, 2H, Bz-H), 7.36-7.40 (m, 4H, Bz-H), 6.45 (s, 1H, H1'), 5.56 (s, 1H, H2'), 4.48 (d, J=3.2 Hz, 1H, H3'), 4.20-4.31 (m, 2H, H4'), 0.77 (s, 9H, C(CH$_3$)$_3$), 0.07 (s, 3H, SiCH$_3$), −0.02 (s, 3H, SiCH$_3$);

$^{13}$C NMR (75 MHz, CDCl$_3$): δ 164.7 (C=O), 152.3 (C-2), 151.2 (C-4), 149.2 (C-6), 141.6 (C-8), [133.5, 133.5, 132.2, 129.5, 128.3, 128.3, 127.6 (Ph)], 122.9 (C-5), 87.8 (C-1'), 82.3 (C-2'), 76.3 (C-4'), 74.8 (C-3'), 25.3 [C(CH$_3$)$_3$], 17.6 [C(CH$_3$)$_3$], −5.2 (SiCH$_3$), −5.6 (SiCH$_3$); HRMS: [M+H]$^+$ calculated for C$_{29}$H$_{34}$N$_5$O$_5$Si, 560.2324; found, 560.2330.

Example 8: Synthesis of 1'α-(Thymin-1-yl)-2'-O-benzoyl-3'-O-tert-butyldimethylsilyl-L-threose (5)

A solution of 3 (10.38 g, 27.3 mmol) and thymine (3.44 g, 27.3 mmol) in 79 mL of dry acetonitrile was treated with BSA (13.3 mL, 54.5 mmol) and stirred at 60° C. for 1 hour. TMSOTf (14.8 mL, 81.7 mmol) was added, and the heating was continued of another 2 hours, after which time the reaction was found to be complete. The reaction mixture was cooled to room temperature and poured into an ice-cold 600 ml of sat. aq. NaHCO$_3$ soln./AcOEt 1:1. The organic layer was separated and washed with water and brine, dried over Na$_2$SO$_4$, and concentrated under reduced pressure. The residue was purified by column chromatography (hexane/EtOAc=4:1 to 3:2) to obtain 5 (10.2 g, 83% yield) as a white foam.

$^1$H NMR (300 MHz, CDCl$_3$): δ 9.50 (s, 1H, NH), 8.02-8.05 (m, 2H, Bz-H), 7.56-7.62 (m, 1H, Bz-H), 7.52 (d, J=1.2 Hz, 1H, H6), 7.42-7.47 (m, 2H, Bz-H), 6.19 (d, J=0.9 Hz, 1H, H1'), 5.23 (s, 1H, H2'), 4.36 (d, J=2.6 Hz, 1H, H3'), 4.15-4.23 (m, 2H, H4'), 1.92 (d, J=1.2 Hz, 3H, T CH$_3$), 0.90 (s, 9H, C(CH$_3$)$_3$), 0.16 (s, 3H, SiCH$_3$), 0.15 (s, 3H, SiCH$_3$);

$^{13}$C NMR (75 MHz, CDCl$_3$): δ 165.0 (Bz CO), 164.3 (C-4), 150.4 (C-2), 136.5 (C-6), [133.7, 129.9, 129.8, 128.9, 128.5, 128.5 (Ph)], 110.2 (C-5), 89.6 (C-1'), 82.7 (C-2'), 76.5 (C-3'), 74.7 (C-4'), 28.0 [C(CH$_3$)$_3$[, 25.6 [C(CH$_3$)$_3$], 17.9 [C(CH$_3$)$_3$], 12.6 (T CH$_3$), −4.8 (SiCH$_3$), −5.3 (SiCH$_3$);

HRMS: [M+H]$^+$ calculated for C$_{22}$H$_{31}$N$_2$O$_6$Si, 447.1946; found, 447.1941.

Example 9: Synthesis of 1'α-(N$^6$—Benzoyladenin-9-yl)-2'-O-benzoyl-L-threose (6)

To a solution of compound 4 (11.6 g, 20.7 mmol) in 200 mL of THF at room temperature was added triethylamine trihydrofluoride. The reaction mixture was stirred at room temperature for 24 hours and found to be complete. The solvent was removed. The residue was taken up into 300 mL of ethyl ether, and 200 mL of water was added. The organic layer was separated and washed with brine, dried over Na$_2$SO$_4$, and concentrated under reduced pressure. The residue was purified by column chromatography (50:1 CH$_2$Cl$_2$/MeOH) to obtain 6 (9.0 g, 97% yield) as a white solid.

$^1$H NMR (300 MHz, CDCl$_3$): δ 9.62 (s, 1H, NH), 8.63 (s, 1H, H2), 8.42 (s, 1H, H8), 7.92-7.96 (m, 4H, Bz-H), 7.33-7.56 (m, 10H, Bz-H), 6.67 (d, J=6.9, 1H, OH), 6.21 (s, 1H, H1'), 5.62 (s, 1H, H2'), 4.61 (brs, 1H, H3'), 4.20-4.33 (m, 2H, H4');

$^{13}$C NMR (75 MHz, CDCl$_3$): δ 165.2 (Bz-CO), 164.8 (Bz-CO—NH), 151.7 (C-2), 150.5 (C-4), 149.5 (C-6), 143.0 (C-8), [133.5, 133.1, 132.4, 129.5, 128.3, 128.2, 127.7 (Ph)], 123.0 (C-5), 89.4 (C-1'), 83.4 (C-2'), 75.8 (C-4'), 74.1 (C-3'); HRMS: [M+H]$^+$ calculated for C$_{23}$H$_{20}$N$_5$O$_5$, 446.1459; found, 446.1451.

Example 10: Synthesis of 1'α-(Thymin-1-yl)-2'-O-benzoyl-L-threose (7)

This compound was prepared as described for 6, using 5 (9.5 g, 21.3 mmol) as starting material. Column chromatographic purification (50:1 CH$_2$Cl$_2$/MeOH) gave compound 7 (7.0 g, 99% yield) as a colourless solid.

$^1$H NMR (300 MHz, CDCl$_3$): δ 9.93 (s, 1H, NH), 7.96-7.98 (m, 2H, Bz-H), 7.52-7.57 (m, 1H, Bz-H), 7.47 (d, J=0.9 Hz, 1H, H6), 7.37-7.42 (m, 2H, Bz-H), 5.99 (d, J=1.2 Hz, 1H, H1'), 5.48 (s, 1H, H2'), 4.77 (brs, 1H, OH), 4.47 (brs, 1H, H3'), 4.31 (d, J=10.0 Hz, H4a'), 4.16 (dd, J=10.0, 3.6 Hz, H4b'), 1.80 (s, 3H, T CH$_3$);

$^{13}$C NMR (75 MHz, CDCl$_3$): δ 165.5 (Bz CO), 164.4 (C-4), 150.5 (C-2), 137.2 (C-6), 133.6, 129.7, 128.6, 128.4, 109.9 (C-5), 90.7 (C-1'), 82.6 (C-2'), 75.51 (C-4'), 73.9 (C-3'), 12.2 (T CH$_3$);

HRMS: [M+H]$^+$ calculated for C$_{16}$H$_{17}$N$_2$O$_6$, 333.1081; found, 333.1082.

Example 11: Synthesis of 1'α-(N$^6$-Benzoyladenin-9-yl)-2'-O-benzoyl-3'-O-diisopropyl-phosphonomethyl-L-threose (8)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

To a solution of 6 (0.345 g, 0.77 mmol) and diisopropylphosphonomethyl trifluoromethanesulfonate (0.254 g, 0.77 mmol) in dry THF (6 mL) was added NaH (60% in oil, 0.102 g, 2.56 mmol) at −10° C. The reaction mixture was warmed to 0° C. and stirred for 0.5 hour. The reaction was quenched with sat. NH$_4$Cl and concentrated. The residue was partitioned between water and EtOAc. The organic layer was washed with brine, dried over Na$_2$SO$_4$, and concentrated under reduced pressure. The residue was purified by chromatography on a silica gel column (50:1 CH$_2$Cl$_2$/MeOH) to afford 8 (0.385 g, 80% yield) as a colourless oil.

$^1$H NMR (300 MHz, CDCl$_3$): δ 9.32 (brs, 1H, NH), 8.80 (s, 1H, H2), 8.51 (s, 1H, H8), 8.03-8.08 (m, 1H, Bz-H), 7.47-7.66 (m, 6H, Bz-H), 6.56 (s, 1H, H1'), 5.80 (s, 1H, H2'), 4.71-4.82 (m, 2H, OCH), 4.49-4.51 (m, 2H, H3' and H4a'), 4.35-4.40 (m, 1H, H4b'), 3.95-4.01 (m, 2H, PCH$_2$), 1.31-1.36 (m, 12H, CH$_3$);
$^{13}$C NMR (75 MHz, CDCl$_3$): δ 165.1 (OBz CO), 164.6 (NBz CO), 152.7 (C-2), 151.5 (C-4), 149.5 (C-6), 141.9 (C-8), 133.9, 133.7, 132.6, 129.9, 128.7, 128.6, 128.4, 127.9, 122.7 (C-5), 87.8 (C-1'), 83.7 (d, $^3J_{P,C}$=9.5 Hz, C-3'), 80.2 (C-2'), 73.5 (C-4'), 71.5 [CH(CH$_3$)$_2$], 71.4 [CH(CH$_3$)$_2$], 64.6 (d, $^1J_{P,C}$=169.4 Hz, PCH$_2$), (24.0, 23.9) [CH(CH$_3$)$_2$];
$^{31}$P NMR (121 MHz, CDCl$_3$): δ 17.8;
HRMS: [M+H]$^+$ calculated for C$_{30}$H$_{35}$N$_5$O$_8$P, 624.2218; found, 624.2217.

Example 12: Synthesis of 1'α-(Thymin-1-yl)-2'-O-benzoyl-3'-O-diisopropyl-phosphonomethyl-L-threose (9)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

To a solution of 7 (2.0 g, 6.02 mmol) and diisopropylphosphonomethyl trifluoromethanesulfonate (1.1 g, 6.62 mmol) in dry THF was added NaH (60% in oil, 0.794 g, 19.86 mmol) at 0° C. The reaction mixture was stirred at 0° C. for 20 minutes. The reaction was quenched with 0.5 ml of acetic acid in ethyl acetate. The residue was partitioned between water and EtOAc. The organic layer was washed with water and brine, dried over Na$_2$SO$_4$, and concentrated under reduced pressure. The residue was purified by chromatography on a silica gel column (40:1 CH$_2$Cl$_2$/MeOH) to afford 9 (2.6 g, 85% yield) as a white solid.

$^1$H NMR (300 MHz, CDCl$_3$): δ 9.25 (brs, 1H, NH), 8.01-8.04 (m, 2H, Bz-H), 7.58-7.60 (m, 1H, Bz-H), 7.43-7.48 (m, 3H, Bz-H and H6), 6.26 (d, J=1.5 Hz, 1H, H1'), 5.39 (s, 1H, H2'), 4.74-4.81 (m, 2H, CH(CH$_3$)$_2$), 4.39 (d, J=10.7 Hz, 1H, H4a'), 4.26 (d, J=3.6 Hz, H3'), 4.13 (dd, J=10.7, 3.7 Hz, H4b'), 3.88-4.06 (m, 2H, PCH$_2$), 1.97 (d, J=0.9 Hz, 3H, T CH$_3$), 1.32-1.35 (m, 12H, CH(CH$_3$)$_2$);
$^{13}$C NMR (75 MHz, CDCl$_3$): δ 165.2 (Bz CO), 163.8 (C-4), 150.4 (C-2), 136.0 (C-6), 133.8, 129.8, 128.5, 111.3 (C-5), 89.0 (C-1'), 83.7 (d, $^3J_{P,C}$=10.9 Hz, C-3'), 80.2 (C-2'), 72.7 (C-4), [71.4, 71.3 CH(CH$_3$)$_2$], 64.5 (d, $^1J_{P,C}$=168.6 Hz, PCH$_2$), [23.9, 23.9 CH(CH$_3$)$_2$], 12.5 (T CH$_3$);
$^{31}$P NMR (121 MHz, CDCl$_3$): δ 17.9;
HRMS: [M+H]$^+$ calculated for C$_{23}$H$_{32}$N$_2$O$_9$P, 511.1840; found, 511.1853.

Example 13: Synthesis of 1'α-(N$^6$-Benzoyladenin-9-yl)-3'-O-diisopropyl-phosphonomethyl-L-threose (10)

To a suspension of 8 (8.65 g, 13.87 mmol) of in 280 ml of THF/MeOH/H$_2$O 5:4:1 at 0° C. was added 6.94 ml (13.87 mmol) of 2N aqueous NaOH. After 20 min, the soln. was neutralized with 2 aq. HCl. The mixture was concentrated under reduced pressure. The residue was partitioned between water and EtOAc. The organic layer was washed with water and brine, dried over Na$_2$SO$_4$, and concentrated under reduced pressure. The residue was purified by chromatography on a silica gel column (30:1 CH$_2$Cl$_2$/MeOH) to afford 10 (5.7 g, 80% yield) as a white solid.

$^1$H NMR (300 MHz, CDCl$_3$): δ 9.53 (brs, 1H, NH), 8.66 (s, 1H, H2), 8.36 (1H, H8), 7.98-8.00 (m, 2H, Bz-H), 7.44-7.58 (m, 3H, Bz-H), 6.21 (d, J=1.7 Hz, 1H, H1'), 4.80 (s, 1H, H2'), 4.63-4.73 (2H, CH(CH$_3$)$_2$), 4.28-4.34 (m, 3H, H4' and H3'), 3.82 (d, J=8.8 Hz, 2H, PCH$_2$), 1.24-1.31 (m, 12H, CH(CH$_3$)$_2$);
$^{13}$C NMR (75 MHz, CDCl$_3$): δ 164.8 (Bz CO), 152.1 (C-2), 151.2 (C-4), 149.1 (C-6), 142.1 (C-8), [133.4, 132.5, 128.5, 127.8 (Ph)], 122.7 (C-5), 90.5 (C-1'), 85.9 (d, $^3J_{P,C}$=9.7 Hz, C-3'), 78.9 (C-2'), 72.5 (C-4'), [71.4, 71.4 CH(CH$_3$)$_2$], 64.4 (d, $^1J_{P,C}$=169.5 Hz, PCH$_2$), [23.8, 23.8, 23.7, 23.7 CH(CH$_3$)$_2$];
$^{31}$P NMR (121 MHz, CDCl$_3$): δ 18.4;
HRMS: [M+H]$^+$ calculated for C$_{23}$H$_{31}$N$_5$O$_7$P, 520.1955; found, 520.1961.

Example 14: Synthesis of 1'α-(Thymin-1-yl)-3'-O-diisopropylphosphonomethyl-L-threose (11)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

A solution of 9 (0.186 g, 0.364 mmol) in 0.4 mL of acetonitrile was treated with LiOH (8.7 mg, 0.364 mmol) in 0.2 mL of water and 0.4 mL of MeOH. The reaction mixture was stirred at room temperature for 0.5 hour and the reaction mixture was neutralized with acetic acid. The solvent was removed and the residue was partitioned between water and EtOAc.

The organic layer was washed with water and brine, dried over Na$_2$SO$_4$, and concentrated under reduced pressure. The residue was purified by chromatography on a silica gel column (20:1 CH$_2$Cl$_2$/MeOH) to afford 11 (126 mg, 85% yield) as a white foam.

$^1$H NMR (300 MHz, CDCl$_3$): δ 10.59 (brs, 1H, NH), 7.41 (d, J=1.2 Hz, H6), 5.84 (s, 1H, H1'), 5.67 (brs, 1H, OH), 4.64-4.77 [m, 2H, CH(CH$_3$)$_2$], 4.39 (s, 1H, H2'), 4.26-4.36 (m, 2H, H4'), 4.14 (d, J=2.4 Hz, H3'), 3.75 (d, J=9.1 Hz, 2H, PCH$_2$), 1.93 (d, J=1.0 Hz, 3H, T CH$_3$), 1.28-1.33 [m, 12H, CH(CH$_3$)$_2$];
$^{13}$C NMR (75 MHz, CDCl$_3$): δ 164.6 (C-4), 151.0 (C-2), 136.4 (C-6), 110.0 (C-5), 93.0 (C-1'), 85.2 (d, $^3J_{P,C}$=10.7 Hz, C-3'), 78.6 (C-2'), 73.6 (C-4'), 71.3 (CH(CH$_3$)$_2$), 71.2 (CH(CH$_3$)$_2$), 64.3 (d, $^1J_{P,C}$=168.4 Hz, PCH$_2$), 24.0 [CH(CH$_3$)$_2$], 23.94 [CH(CH$_3$)$_2$], 23.89 [CH(CH$_3$)$_2$], 23.82 [CH(CH$_3$)$_2$], 12.43 (T CH$_3$);

$^{31}$P NMR (121 MHz, CDCl$_3$): δ 18.27;
HRMS: [M+H]$^+$ calculated for C$_{16}$H$_{28}$N$_2$O$_8$P, 407.1578; found, 407.1582.

Example 15: Synthesis of 1'α-(N$^6$-Benzoyladenin-9-yl)-2'-deoxy-3'-O-diisopropyl-phosphonomethyl-L-threose (12)

To a solution of compound 10 (137 mg, 0.26 mmol) and DMAP (10 mg, 0.08 mmol) in dried CH$_2$Cl$_2$ (2.70 mL) was added 1,1'-thiocarbonyldiimidazole (TCD) (94 mg, 0.53 mmol) at room temperature. The reaction mixture was refluxed for overnight. The mixture was washed with brine, dried over Na$_2$SO$_4$, concentrated under reduced pressure. To the residue in toluene (5 ml) was added azobisisobutyronitrile (AIBN) (17 mg, 0.11 mmol) and tributytin hydride (0.28 ml, 1.05 mmol). The reaction mixture was refluxed for 20 minutes, the reaction was found complete. The solvent was removed under reduced pressure and the residue was purified by chromatography on a silica gel column (30:1 CH$_2$Cl$_2$/MeOH) to afford 12 (130 mg, 98% yield) as a white solid.

$^1$H NMR (500 MHz, CDCl$_3$): δ 9.15 (s, 1H, NH), 8.79 (s, 1H, H2), 8.49 (s, 1H, H8), 8.00-8.02 (m, 2H, Bz-H), 7.57-7.59 (m, 1H, Bz-H), 7.50-7.53 (m, 2H, Bz-H), 6.55 (dd, J=7.7, 2.0 Hz, 1H, H1'), 4.69-4.75 [m, 2H, CH(CH$_3$)$_2$], 4.51-4.53 (m, 1H, H3'), 4.38 (d, J=10.5 Hz, 1H, H4a'), 4.08 (dd, J=10.5, 4.1 Hz, 1H, H4b'), 3.67-3.75 (m, 2H, PCH$_2$), 2.62-2.74 (m, 2H, H2'). 1.28-1.33 [m, 12H, CH(CH$_3$)$_2$].

$^{13}$C NMR (125 MHz, CDCl$_3$): δ 164.5 (Bz CO), 152.5 (C-2), 151.5 (C-4), 149.3 (C-6), 142.1 (C-8), [133.8, 132.6, 128.8, 127.8 (Ph)], 122.8 (C-5), 83.7 (C-1'), 80.2 (d, $^3J_{P,C}$=9.5 Hz, C-3'), 73.9 (C-4'), [71.3, 71.3 (CH(CH$_3$)$_2$], 64.0 (d, $^1J_{P,C}$=169.2 Hz, PCH$_2$), 38.6 (C-2'), 24.0 (CH(CH$_3$)$_2$);

$^{31}$P NMR (121 MHz, CDCl$_3$): δ 18.2;
HRMS: [M+H]$^+$ calculated for C$_{23}$H$_{31}$N$_5$O$_6$P, 504.2006; found, 504.2023.

Example 16: Synthesis of 1'α-(Thymin-1-yl)-2'-deoxy-3'-O-diisopropyl-phosphonomethyl-L-threose (13)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

This compound was prepared as described for 12, using 11 (1.53 g, 3.77 mmol) as starting material. Column chromatographic purification (25:1 CH$_2$Cl$_2$/MeOH) gave compound 13 (1.44 g, 97% yield) as a white solid.

$^1$H NMR (300 MHz, CDCl$_3$): δ 8.97 (brs, 1H, NH), 7.55 (d, J=1.2 Hz, 1H, H6), 6.24 (dd, J=8.1, 2.6 Hz, 1H, H1'), 4.69-4.80 [m, 2H, CH(CH$_3$)$_2$], 4.30-4.36 (m, 2H, H4a' and H3'), 3.84 (dd, J=10.8, 3.6 Hz, H4b'), 3.71 (d, J=9.2 Hz, PCH$_2$), 2.50-2.60 (m, 1H, H2a'), 2.16 (d, J=15.3 Hz, 1H, H2b'), 1.97 (d, J=1.1 Hz, T CH$_3$), 1.31-1.35 (m, 12H, CH(CH$_3$)$_2$);

$^{13}$C NMR (75 MHz, CDCl$_3$): δ 163.8 (C-4), 150.6 (C-2), 136.4 (C-6), 110.7 (C-5), 84.8 (C-1'), 80.2 (d, $^3J_{P,C}$=11.4 Hz, C-3'), 73.4 (C-4'), 71.2 [CH(CH$_3$)$_2$], 64.0 (d, $^1J_{P,C}$=169.8 Hz, PCH$_2$), 38.3 (C-2'), 24.0 [CH(CH$_3$)$_2$], 12.5 (T CH$_3$);

$^{31}$P NMR (121 MHz, CDCl$_3$): δ 18.2;
HRMS: [M+H]$^+$ calculated for C$_{16}$H$_{28}$N$_2$O$_7$P, 391.1629; found, 391.1628.

Example 17: Synthesis of 1'α-(Adenin-9-yl)-2'-deoxy-3'-O-diisopropyl-phosphonomethyl-L-threose (14)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

A solution of 12 (2.17 g, 4.32 mmol) in sat. NH$_3$ in MeOH (300 mL) was stirred at room temperature overnight. After removing the volatiles, the crude residue was purified by chromatography on silica gel (20:1 CH$_2$Cl$_2$/MeOH) to afford 14 (1.58 g, 92% yield) as a white solid.

$^1$H NMR (300 MHz, CDCl$_3$): δ 8.35 (s, 1H, H8), 8.31 (s, 1H, H2), 6.48 (dd, J=7.5, 2.4 Hz, 1H, H1'), 6.10 (brs, 2H, NH$_2$), 4.71-4.78 (m, 2H, CH(CH$_3$)$_2$), 4.45-4.48 (m, 1H, H3'), 4.36 (d, J=10.5 Hz, 1H, H4a'), 4.06 (dd, J=10.5, 4.3 Hz, 1H, H4b'), 3.71-3.75 (m, 2H, PCH$_2$), 2.57-2.73 (m, 2H, H2'), 1.28-1.35 (m, 12H, CH(CH$_3$)$_2$);

$^{13}$C NMR (75 MHz, CDCl$_3$): δ 155.5 (C-6), 153.0 (C-2), 149.7 (C-4), 139.5 (C-8), 119.5 (C-5), 83.4 (C-1'), 80.5 (d, $^3J_{P,C}$=11.2 Hz, C-3'), 73.7 (C-4'), [71.4, 71.3 (CH(CH$_3$)$_2$], 64.1 (d, $^1J_{P,C}$=169.6 Hz, 2H, PCH$_2$), 38.5 (C-2'), (24.0, 24.0, 23.9 CH(CH$_3$)$_2$];

$^{31}$P NMR (121 MHz, CDCl$_3$): δ 18.2;
HRMS: [M+H]$^+$ calculated for C$_{16}$H$_{27}$N$_5$O$_5$P, 400.1744; found, 400.1746.

Example 18: Synthesis of 1'α-(Adenin-9-yl)-2'-deoxy-3'-O-phosphonomethyl-L-threose triethylammonium salt (15)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

To a solution of 14 (30 mg, 0.075 mmol) and 2,6-lutidine (0.07 mL, 0.60 mmol) in dry CH$_3$CN (3 mL) was added bromotrimethylsilane (0.08 mL, 0.60 mmol) at 0° C. The reaction mixture was stirred at room temperature for 24 hours. The reaction was quenched with 1.0 M TEAB solution (1 mL). The solvent was removed under reduced pressure at rt. The residue was partitioned between water and EtOAc/ether (1:1), the water layer was lyophilized and the residue was purified by column chromatography (10:5:1 CH$_2$Cl$_2$/MeOH/1 M TEAB) to give crude 15. Further purification using preparative reverse phase HPLC with gradient CH$_3$CN in 0.05 M TEAB solution from 2% to 30% gave 15 (19 mg, 60%) as a white foam.

$^1$H NMR (500 MHz, CDCl$_3$): δ 8.55 (s, 1H, H8), 8.15 (s, 1H, H2), 6.35 (dd, J=8.2, 2.2 Hz, 1H, H1'), 4.51-4.53 (m, 1H, H3'), 4.31 (d, J=10.4 Hz, 1H, H4a'), 4.06 (dd, J=10.3, 4.1 Hz, 1H, H4b'), 3.45-3.53 (m, 2H, PCH$_2$), 2.75-2.81 (m, 1H, H2a'), 2.64 (d, J=15.1 Hz, 1H, H2b');

$^{13}$C NMR (125 MHz, CDCl$_3$): δ 155.0 (C-6), 152.0 (C-2), 148.2 (C-4), 140.9 (C-8), 117.9 (C-5), 82.9 (C-1'), 79.0 (d, $^3J_{P,C}$=10.3 Hz, C-3'), 73.3 (C-4'), 66.6 (d, $^1J_{P,C}$=151.3 Hz, PCH$_2$), 36.5 (C-2');

$^{31}$P NMR (121 MHz, D$_2$O): δ 13.1;
HRMS: [M−H]$^−$ calculated for C$_{10}$H$_{13}$N$_5$O$_5$P, 314.0660; found, 314.0657.

Example 19: Synthesis of 1'α-(Thymin-1-yl)-2'-deoxy-3'-O-phosphonomethyl-L-threose triethylammonium salt (16)

This compound was synthesized in analogy to a known procedure (Wu, T.; Froeyen, M.; Kempeneers, V.; Pannecouque, C.; Wang, J.; Busson, R.; De Clercq, E.; Herdewijn, P. *J. Am. Chem. Soc.* 2005, 127, 5056).

To a solution of 13 (205 mg, 0.53 mmol) and 2,6-lutidine (0.49 mL, 4.20 mmol) in dry $CH_3CN$ (20 mL) was added iodotrimethylsilane (0.60 mL, 4.20 mmol) at 0° C. The reaction mixture was stirred for 7 hours. The reaction was quenched with 1.0 M TEAB solution (4 mL). The solvent was removed under reduced pressure at room temperature. The residue was partitioned between water and EtOAc/ether (1:1), the water layer was lyophilized and the residue was purified by column chromatography (10:5:1 $CH_2Cl_2$/MeOH/1 M TEAB) to give crude 16. Further purification using preparative reverse phase HPLC with gradient $CH_3CN$ in 0.05 M TEAB solution from 2% to 30% gave 16 (138 mg, 65%) as a white foam.

$^1$H NMR (300 MHz, $D_2O$): δ 7.70 (s, 1H, H6), 6.11 (d, J=6.3 Hz, 1H, H1'), 4.30 (brs, 2H, H4a' and H3'), 3.86 (d, J=7.5 Hz, H4b'), 3.51 (d, J=9.1 Hz, $PCH_2$), 2.50-2.55 (m, 1H, H2a'), 2.20 (d, J=15.1 Hz, 1H, H2b'), 1.82 (s, 3H, T $CH_3$);

$^{13}$C NMR (75 MHz, $CDCl_3$): δ 166.3 (C-4), 151.4 (C-2), 138.2 (C-6), 110.7 (C-5), 85.1 (C-1'), 79.4 (d, $^3J_{P,C}$=11.5 Hz, C-3'), 73.4 (C-4'), 64.6 (d, $^1J_{P,C}$=157.6 Hz, $PCH_2$), 36.4 (C-2'), 11.4 (T $CH_3$);

$^{31}$P NMR (121 MHz, $CDCl_3$): δ 15.3;

HRMS: [M−H]$^-$ calculated for $C_{10}H_{14}N_2O_7P$, 305.0544; found, 305.0555.

Example 20: Synthesis of Phenylalanine n-propyl ester hydrochloride

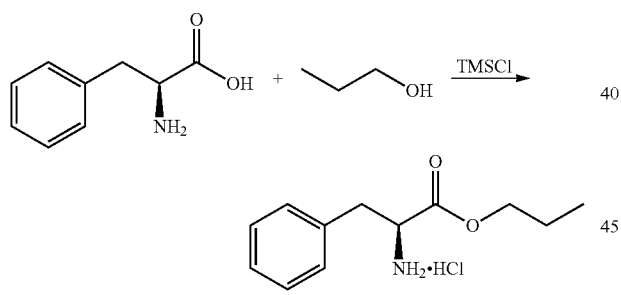

This compound was synthesized according to a known procedure: Li, G.; Sha, Y. *Molecules* 2008, 13, 1111.

To a mixture of phenylalanine (1.0 g, 6.05 mmol) and n-propanol (11 mL) was added chlorotrimethylsilane (2.30 mL, 18.15 mmol) at 0° C. The reaction mixture was raised to room temperature and stirred overnight. After the completion of reaction (as monitored by NMR), the reaction mixture was concentrated on a rotary evaporator. To the residue was added 50 mL of diethyl ether and the mixture was filtered and the filter cake was dried to give the phenylalanine n-propyl ester hydrochloride (1.38 g, 93%).

$^1$H NMR (300 MHz, DMSO): δ 8.77 (s, 3H), 7.24-7.33 (m, 5H), 4.21 (t, J=5.9 Hz, 1H), 3.98 (dt, J=6.6 Hz, 2.2 Hz, 2H), 3.22-3.88 (m, 1H), 3.02-3.10 (m, 1H), 1.40-1.52 (m, 2H), 0.73-0.79 (m, 3H); $^{13}$C NMR (75 MHz, $CDCl_3$): δ 169.2, 134.9, 129.5, 128.7, 127.3, 67.1, 53.4, 36.1, 21.3, 10.2.

Example 21: Synthesis of Aspartic Acid Isoamyl Ester Hydrochloride

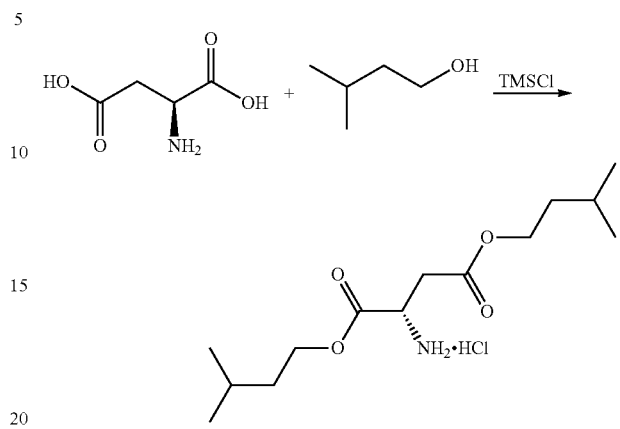

This compound was synthesized according to a known procedure: Li, G.; Sha, Y. *Molecules* 2008, 13, 1111; and Maiti, M.; Maiti, M.; Rozenski, J.; Jonghe, S. D.; Herdewijn, P. *Org. Biomol. Chem.* 2015, DOI: 10.1039/c5ob00427f.

To a mixture of aspartic acid (1.0 g, 7.51 mmol) and isoamylol (39 mL) was added chlorotrimethylsilane (5.72 mL, 45.08 mmol) at 0° C. The reaction mixture was raised to room temperature and stirred for 48 hours. After the completion of reaction (as monitored by NMR), the reaction mixture was concentrated on a rotary evaporator. To the residue was added 50 mL of hexane and the mixture was filtered and the filter cake was dried to give the aspartic acid isoamyl ester hydrochloride (2.1 g, 90%).

$^1$H NMR (300 MHz, DMSO): δ 8.78 (s, 3H), 4.29 (t, J=5.7 Hz, 1H), 4.07-4.24 (m, 4H), 2.93-3.10 (m, 2H), 1.60-1.69 (m, 2H), 1.48 (q, J=6.7 Hz, 4H), 0.86-0.90 (m, 12H);

$^{13}$C NMR (75 MHz, $CDCl_3$): δ 169.1, 168.2, 64.2, 63.3, 48.4, 36.6, 36.5, 34.1, 24.4, 24.1, 22.2, 22.2, 22.1

Example 22: Synthesis of 1'α-(Adenin-9-yl)-2'-deoxy-3'-O—{[N,N'-bis(n-propy-L-phenylalaninate)]methylphosphonobisamidate}-L-threose (PM-DTA bis-Phe-n-propyl ester; compound 17)

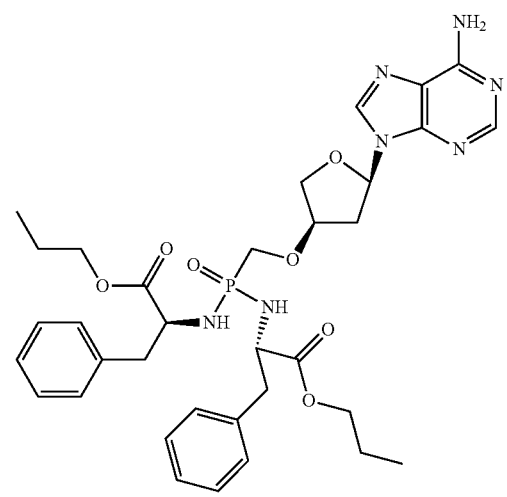 [SMILES: CCCOC(=O)[C@H](Cc1ccccc1)NP(=O)(CO[C@H]1CO[C@@H](n2cnc3c(N)ncnc32)C1)N[C@@H](Cc1ccccc1)C(=O)OCCC]

This compound was synthesized similarly to a known procedure (Mackman, R. L., Ray, A. S., Hui, H. C., Zhang, L., Birkus, G., Boojamra C. G., Desai, M. C, Douglas, J. L., Gao, Y., Grant, D., Laflamme, G., Lin, K. Y., Markevitch, D. Y., Mishra, R., McDermott, M., Pakdaman, R., Petrakovsky, O. V., Vela, J. E., Cihlar, T. *Bioorg. Med. Chem.* 2010, 18, 3606-3617) for preparing prodrugs of the nucleoside phosphonate HIV reverse transciptase inhibitor GS-9148.

The mixture of PMDTA (23 mg, 0.055 mmol, Et$_3$N salt) and (S)-phenylalanine-O-n-Pr ester hydrochloride (81 mg, 6 equiv, 0.331 mmol) was co-evaporated with anhydrous pyridine (2 mL×3) and then dissolved again in anhydrous pyridine (1 mL) containing Et$_3$N (92 µL, 0.662 mmol). The resultant mixture was stirred at 60° C. under argon. In a separate flask, 2,2'-dithiodipyridine (85 mg, 0.387 mmol) and PPh$_3$ (101 mg, 0.387 mmol) were dissolved in anhydrous pyridine (1 mL) which was stirred at room temperature for 15 min to give a light yellow solution, this reagent solution was then added to the solution of PMDTA in one portion. The reaction mixture was stirred overnight at 60° C. under argon. The reaction mixture was then concentrated under reduced pressure. The resultant residue was first purified by silica gel chromatography (60:1 to 20:1 DCM/MeOH) and then purified by preparative reverse phase HPLC (linear gradient, 5-95% CH$_3$CN in water to give the phosphonic diamide pro-drug 17 as a white solid (28 mg, 73%).

$^1$H NMR (500 MHz, acetone-d$_6$): δ 8.47 (s, 1H, H8), 8.20 (s, 1H, H2), 7.18-7.29 (m, 10H, Ph-H), 6.42-6.44 (m, 1H, H1'), 4.2-4.35 (m, 3H, Phe-CH, H3', H4a'), 4.04-4.15 (m, 1H, Phe-CH), 3.95-4.03 (m, 5H, OCH$_2$CH$_2$CH$_3$, H4b'), 3.85-3.95 (m, 1H, Phe-NH), 3.47-3.49 (m, 2H, PCH$_2$), 3.35-3.45 (m, 1H, Phe-NH), 2.80-3.15 (m, 4H, Ph-CH$_2$), 2.68-2.75 (m, 1H, H2a'), 2.40-2.45 (m, 1H, H2b'), 1.55-1.64 (m, 4H, OCH$_2$CH$_2$CH$_3$), and 0.90-0.91 (OCH$_2$CH$_2$CH$_3$);

$^{13}$C NMR (125 MHz, acetone-d$_6$): δ (173.9, 173.4) (Phe-CO), 157.1 (C-6), 153.7 (C-2), 150.6 (C-4), 140.7 (C-8), (138.3, 137.9, 130.6, 130.6, 129.1, 129.0, 127.4, 127.3) (Ph), 119.9 (C-5), 83.9 (C-1'), 81.4 (d, $^3J_{P,C}$=13.8 Hz, C-3'), 74.1 (C-4'), [67.1, 67.1 (OCH$_2$CH$_2$CH$_3$)], 66.9 (d, $^1J_{P,C}$=136.3 Hz), [55.3, 54.7 (Phe-CH)], [41.3, 41.2 (Ph-CH$_2$)], 38.9 (C-2'), 22.6 (OCH$_2$CH$_2$CH$_3$), 13.8 (OCH$_2$CH$_2$CH$_3$);

$^{31}$P NMR (121 MHz, acetone-d$_6$): δ 19.7;

HRMS: [M+H]$^+$ calculated for C$_{34}$H$_{45}$N$_7$O$_7$P, 694.3112; found, 694.3120.

Example 23: 1'α-(Adenin-9-yl)-2'-deoxy-3'-O—{[N-(isopropyl-L-alaninate)](phenoxy)-methyl-phosphonoamidate]}-L-threose (PMDTA Ala-isopropyl, OPh ester; compound 18)

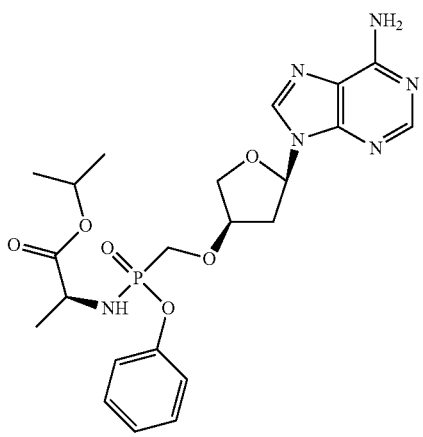 [SMILES: CC(C)OC(=O)[C@H](C)NP(=O)(CO[C@H]1CO[C@@H](n2cnc3c(N)ncnc32)C1)Oc1ccccc1]

This compound was synthesized similarly to a known procedure (Mackman, R. L., Ray, A. S., Hui, H. C., Zhang, L., Birkus, G., Boojamra C. G., Desai, M. C, Douglas, J. L., Gao, Y., Grant, D., Laflamme, G., Lin, K. Y., Markevitch, D. Y., Mishra, R., McDermott, M., Pakdaman, R., Petrakovsky, O. V., Vela, J. E., Cihlar, T. *Bioorg. Med. Chem.* 2010, 18, 3606-3617) for preparing prodrugs of the nucleoside phosphonate HIV reverse transciptase inhibitor GS-9148.

The mixture of PMDTA (28 mg, 0.067 mmol, Et$_3$N salt), alanine isopropyl ester HCl salt (23 mg, 2 equiv, 0.134 mmol) and PhOH (32 mg, 5 equiv, 0.336 mmol) was co-evaporated with anhydrous pyridine (2 mL×3) and then dissolved again in anhydrous pyridine (1 mL) containing Et$_3$N (112 µL, 0.804 mmol). The mixture was stirred at 60° C. under argon. In a separate flask, 2,2'-dithiodipyridine (123 mg, 0.558 mmol) was mixed with PPh$_3$ (106 mg, 0.403 mmol) in anhydrous pyridine (1 mL) and the resultant mixture was stirred at room temperature for 15 minutes to give a light yellow solution. This solution was then added to the solution of PMDTA in one portion. The reaction mixture was stirred overnight at 60° C. The reaction mixture was concentrated under reduced pressure. The resultant residue was first purified by silica gel chromatography (60:1 to 20:1 DCM/MeOH) and then purified by preparative reverse phase HPLC (linear gradient, 5-95% CH$_3$CN in water) to give the phosphonic monoamidate pro-drug 18 (16 mg, 47%) as white solid and a mixture of P(R) and P(S) isomers.

$^1$H NMR (500 MHz, acetone-d$_6$): δ 8.44 (s, 1H, H8), 8.20 (s, 1H, H2), 7.16-7.36 (m, 5H, Ph-H), 6.45-6.47 (m, 1H, H1'), 4.89-4.95 (m, 1H, CH(CH$_3$)$_2$), 4.66-4.85 (m, 1H, Ala-NH), 4.52-4.56 (m, 1H, H3'), 4.37-4.42 (m, 1H, H4a'), 4.02-4.08 (m, 4H, H4b', PCH$_2$, Ala-CH), 2.76-2.84 (m, 1H, H2a'), 2.56-2.63 (m, 1H, H2b'), 1.25-1.28 (m, 3H, Ala-CH$_3$), 1.15-1.19 (m, 6H, CH(CH$_3$)$_2$);

$^{13}$C NMR (125 MHz, acetone-d$_6$): δ [174.1, 173.7 (Ala-CO)], 157.0 (C-6), [153.7, 153.6 (C-2)], [151.73, 151.55 (Ph)], [150.62, 150.59 (C-4)] [140.57, 140.48 (C-8)], [130.38, 130.31, 125.32, 125.29, 121.77, 121.73, 121.67, 121.64 (Ph)], [120.02, 119.98 (C-5)], [84.22, 83.90 (C-1')], [81.88, 81.85 (d, $^3J_{P,C}$=13.44, 13.03 Hz, C-3')], [74.36, 73.90 (C-4')], [69.14, 69.08 (CH(CH$_3$)$_2$], [65.99, 65.91 (d, $^1J_{P,C}$=156.5, 155.7 Hz, PCH$_2$)], [50.53, 50.43 (Ala-CH)], [39.10, 39.07 (C-2')], [21.84, 21.81 (CH(CH$_3$)$_2$)], [21.27, 20.95 (Ala-CH$_3$)];

$^{31}$P NMR (121 MHz, acetone-d$_6$): δ 21.6, 21.6;

HRMS: [M+H]$^+$ calculated for C$_{22}$H$_{30}$N$_6$O$_6$P, 505.1959; found, 505.1965.

Example 24: Synthesis of 1'α-(Adenin-9-yl)-2'-deoxy-3'-O—{[N-(diisoamyl-L-aspartate)](phenoxy)methylphosphonoamidate}-L-threose (PMDTA Asp-iso-amyl, OPh ester; compound 19)

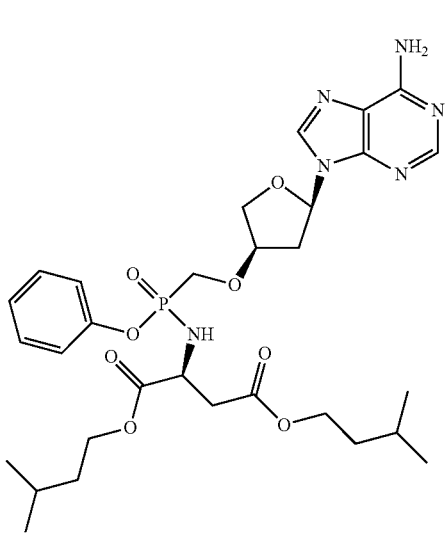 [SMILES: CC(C)CCOC(=O)C[C@H](NP(=O)(CO[C@H]1CO[C@@H](n2cnc3c(N)ncnc32)C1)Oc1ccccc1)C(=O)OCCC(C)C]

This compound was prepared as described for pro-drug 18. Yield=66%.

$^1$H NMR (500 MHz, acetone-d$_6$): δ 8.40 (s, 1H, H8), 8.19 (s, 1H, H2), 7.14-7.37 (m, 5H, Ph-H), 6.70 (brs, 2H, NH$_2$), 6.44-6.47 (m, 1H, H1'), 4.73-4.87 (m, 1H, Asp-NH), 4.51-4.57 (m, 1H, H3'), 4.36-4.42 (m, 2H, H4a', Asp-CH), 3.97-4.12 [m, 7H, H4b', PCH$_2$, OCH$_2$CH$_2$CH(CH$_3$)$_2$], 2.53-2.84 (m, 4H, Asp-CH$_2$, H2'), 1.58-1.68 (m, 2H, OCH$_2$CH$_2$CH(CH$_3$)$_2$), 1.42-1.50 (m, 4H, OCH$_2$CH$_2$CH(CH$_3$)$_2$), 0.86-0.89 (m, 12H, OCH$_2$CH$_2$CH(CH$_3$)$_2$);

$^{13}$C NMR (125 MHz, acetone-d$_6$): δ [172.7, 172.4, 171.1 (Asp-CO)], [157.0, 156.9 (C-6)], [153.7, 153.64 (C-2)], [151.68, 151.66 (Ph)], 150.63 (C-4), [140.58, 140.45 (C-8)], [130.4, 130.3, 125.40, 125.38, 121.82, 121.78, 121.72, 121.68 (Ph)], [120.06, 120.00 (C-5)], [84.2, 83.9 (C-1')], 81.9 (d, $^3J_{P,C}$=13.5 Hz, C-3'), [74.4, 73.9 (C-4')], [65.94, 65.90 (d, $^1J_{P,C}$=156.6, 155.9 Hz, PCH$_2$)], [64.55, 64.45, 63.8 (OCH$_2$CH$_2$CH(CH$_3$)$_2$)], [51.54, 51.46 (Asp-CH)], [39.55, 39.10 (Asp-CH$_2$)], [37.93, 37.90, 37.87 (OCH$_2$CH$_2$CH(CH$_3$)$_2$)], [25.64, 25.62, 25.55, 25.53 (OCH$_2$CH$_2$CH(CH$_3$)$_2$)], [22.66, 22.61 (OCH$_2$CH$_2$CH(CH$_3$)$_2$)];

$^{31}$P NMR (121 MHz, acetone-d$_6$): δ 21.16, 21.15;

HRMS: [M+H]$^+$ calculated for C$_{30}$H$_{44}$N$_6$O$_8$P, 647.2953; found, 647.2953.

Example 25: Synthesis of 1'α-(Thymin-1-yl)-2'-deoxy-3'-O—[N, N'-bis(n-propyl-L-phenylalaninate)) methylphosphonobisamidate]-L-threose (PMDTT bis-Phe-n-propyl ester; compound 20)

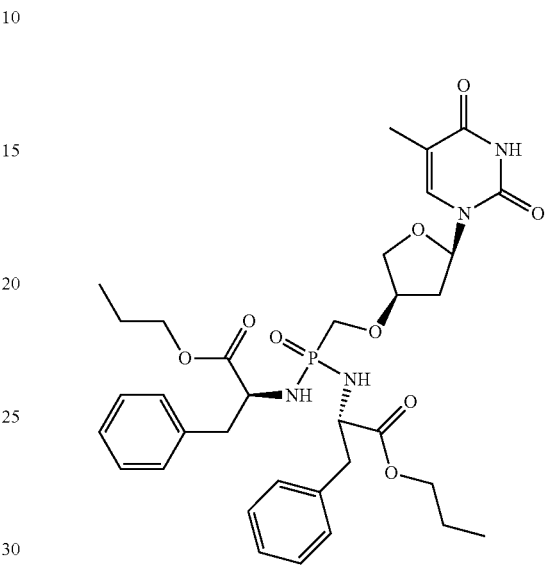

Yield=34%. This compound was prepared as described for pro-drug 17.

$^1$H NMR (500 MHz, acetone-d$_6$): δ 9.92 (s, 1H, NH), 7.61-7.62 (m, 1H, H6), 7.20-7.29 (m, 10H, Ph-H), (6.16, 6.15) (d, J=2.8 Hz, 1H, H1'), 4.09-4.28 (m, 4H, H3', H4a' and Phe-CH), 3.98-4.05 (m, 4H, OCH$_2$CH$_2$CH$_3$), 3.74-3.80 (m, 2H, NH and H4b'), 3.44-3.49 (m, 1H, NH), 3.38 (dd, J=8.7, 1.1 Hz, 2H, PCH$_2$), 2.82-3.08 (m, 4H, Phe-CH$_2$), 2.52-2.57 (m, 1H, H2a'), 2.00-2.06 (m, 1H, H2b'), 1.84 (d, J=1.2 Hz, 3H, T CH$_3$), 1.57-1.66 (m, 4H, OCH$_2$CH$_2$CH$_3$), 0.86-0.93 (m, 6H, OCH$_2$CH$_2$CH$_3$);

$^{13}$C NMR (125 MHz, acetone-d$_6$): δ [173.6, 173.3 (Phe-CO)], 164.2 (C-4), 151.3 (C-2), [138.0, 137.8 (Ph)], 137.2 (C-6), [130.4, 130.3, 128.90, 128.86, 127.30, 127.27 (Ph)], 110.5 (C-5), 85.1 (C-1'), 80.9 (d, $J_{P,C}$=12.1 Hz, C-3'), 73.4 (C-4'), [66.94, 66.92 (OCH$_2$CH$_2$CH$_3$)], 66.6 (PCH$_2$, $^1J_{P,C}$=136.9 Hz), [54.93, 54.64 (Phe-CH)], [41.2, 41.0 (Phe-CH$_2$)], 38.3 (C-2'), [22.39, 22.34 (OCH$_2$CH$_2$CH$_3$)], 12.4 (T CH$_3$), [10.45, 10.41 (OCH$_2$CH$_2$CH$_3$)].

$^{31}$P NMR (121 MHz, acetone-d$_6$): δ 19.6.

HRMS: [M+H]$^+$ calculated for C$_{34}$H$_{46}$N$_4$O$_9$P, 685.2997; found, 685.3006.

Example 26: Synthesis of 1'α-(Thymin-1-yl)-2'-deoxy-3'-O—{[N-(isopropyl-L-alaninate)](phenoxy)methylphosospnoamidate}-L-threose (PMDTT Ala-$^i$propyl, OPh ester; compound 21)

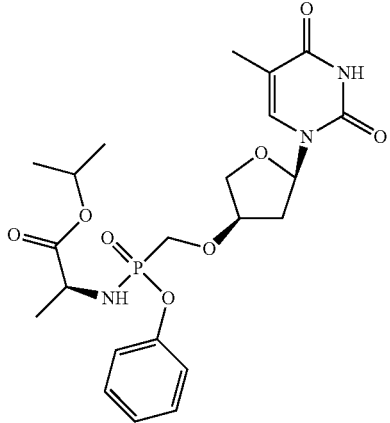 [SMILES: Cc1cn([C@H]2C[C@@H](OCP(=O)(N[C@@H](C)C(=O)OC(C)C)Oc3ccccc3)CO2)c(=O)[nH]c1=O]

This compound was prepared as described for pro-drug 18. Yield=41%.
$^1$H NMR (500 MHz, acetone-d$_6$): δ 9.91 (s, 1H, NH), 7.68-7.69 (m, 1H, H6), 7.16-7.35 (m, 5H, Ph-H), 6.20-6.23 (m, 1H, H1'), 4.92-4.94 (m, 1H, CH(CH$_3$)$_2$), 4.59-4.71 (m, 1H, NH), 4.39-4.44 (m, 1H, H3'), 4.34-4.38 (m, 1H, H4a'), 3.96-4.05 (m, 3H, Ala-CH and PCH$_2$), 3.82-3.87 (m, 1H, H4b'), 2.60-2.66 (m, 1H, H2a'), 2.14-2.20 (m, 1H, H2b'), 1.80-1.81 (m, 3H, T CH$_3$), 1.25-1.30 (m, 3H, Ala-CH$_3$), 1.18-1.20 [m, 6H, CH(CH$_3$)$_2$];
$^{13}$C NMR (125 MHz, acetone-d$_6$): δ 174.0, 173.7 (Ala-CO), 164.4 (C-4), [151.6, 151.5 (C-2)], [137.47, 137.42 (C-6)], [130.34, 130.30, 125.36, 125.33, 121.78, 121.75, 121.64, 121.60 (Ph)], [110.64, 110.60 (C-5)], [85.35, 85.26 (C-1')], 81.6 (d, $^3J_{P,C}$=12.6 Hz, C-3'), [73.9, 73.6 (C-4')], [69.15, 69.13 (OCH(CH$_3$)$_2$)], [66.84, 65.79 (PCH$_2$, $^1J_{P,C}$=155.8, 156.4 Hz)], [50.48, 50.44 (Ala-CH)], 38.5 (C-2'), [21.87, 21.84, 21.80 (OCH(CH$_3$)$_2$)], [21.3, 21.2 (Ala-CH$_3$)], 12.60 (T CH$_3$);
$^{31}$P NMR (121 MHz, acetone-d$_6$): δ 21.63, 20.69;
HRMS: [M+H]$^+$ calculated for C$_{22}$H$_{31}$N$_3$O$_8$P, 496.1843; found, 496.1850.

Example 27: Synthesis of 1'α-(Thymin-1-yl)-2'-deoxy-3'-{[N-(diisoamyl-L-aspartate)](phenoxy)methylphosphonoamidate}-L-threose (PMDTT Asp-iso-amyl, OPh ester; compound 22)

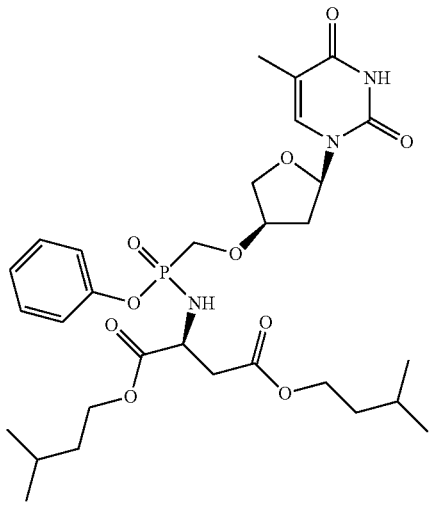 [SMILES: Cc1cn([C@H]2C[C@@H](OCP(=O)(N[C@@H](CC(=O)OCCC(C)C)C(=O)OCCC(C)C)Oc3ccccc3)CO2)c(=O)[nH]c1=O]

This compound was prepared as described for pro-drug 18. Yield=60%.
$^1$H NMR (500 MHz, acetone-d$_6$): δ 10.00 (s, 1H, NH), 7.68-7.69 (m, 1H, H6), 7.17-7.35 (m, 5H, Ph-H), 6.21-6.23 (m, 1H, H1'), 4.73-4.86 (m, 1H, NH), 4.34-4.46 (m, 3H, H3', H4a' and Asp-CH), 4.02-4.17 [m, 6H, PCH$_2$ and OCH$_2$CH$_2$CH(CH$_3$)$_2$], 3.81-3.87 (m, 1H, H4b'), 2.78-2.82 (m, 2H, Asp-CH$_2$), 2.60-2.65 (m, 1H, H2a'), 2.12-2.20 (m, 1H, H2b'), 1.80-1.81 (m, 3H, T CH$_3$), 1.62-1.69 [m, 2H, OCH$_2$CH$_2$CH(CH$_3$)$_2$], 1.44-1.51 [m, 4H, OCH$_2$CH$_2$CH(CH$_3$)$_2$], 0.88-0.90 [m, 12H, OCH$_2$CH$_2$CH(CH$_3$)$_2$];
$^{13}$C NMR (125 MHz, acetone-d$_6$): δ [172.5, 172.4, 171.09, 171.03 (Asp-CO)], 164.4 (C-4), 151.5 (C-2), [137.45, 137.41 (C-6)], [130.33, 130.31, 125.44, 125.42, 121.80, 121.77, 121.67, 121.64 (Ph)], [110.74, 110.67 (C-5)], [85.29, 85.20 (C-1')], [81.7, 81.6 (C-3')], [73.9, 73.5 (C-4')], [65.68, 64.84 (PCH$_2$, $^1J_{P,C}$=155.5, 157.0 Hz)], [64.51, 64.47, 63.80 (OCH$_2$CH$_2$CH(CH$_3$)$_2$)], 51.4 (Asp-CH), [25.63, 25.54 (OCH$_2$CH$_2$CH(CH$_3$)$_2$)], 22.7 (OCH$_2$CH$_2$CH(CH$_3$)$_2$), 12.6 (T CH$_3$);
$^{31}$P NMR (121 MHz, acetone-d$_6$): δ 22.18, 21.22;
HRMS: [M+H]$^+$ calculated for C$_{30}$H$_{45}$N$_3$O$_{10}$P, 638.2837; found, 638.2820.

Example 28: Synthesis of 1-O-Methyl-2-O-benzoyl-L-threose (23)

To a solution of 2b (8.04 g, 23.75 mmol) in anhydrous methanol (59 mL) was added acetic chloride (1.69 mL, 23.75 mmol). After stirring for 2 hours at room temperature, Et$_3$N (4 mL) was added and the mixture was concentrated under reduced pressure, the residue was partitioned between water and EtOAc. The organic layer was washed with sat. aq. NaHCO$_3$ and brine, dried over Na$_2$SO$_4$, and concentrated under reduced pressure. The residue was purified by column chromatography (3:1 to 2:1, hexane/EtOAc) to afford 23 (4.7 g, 83% yield) as a colorless oil.
$^1$H NMR (300 MHz, CDCl$_3$): δ 8.00-8.06 (m, 2H, Ph), 7.56-7.62 (m, 1H, Ph), 7.42-7.48 (m, 2H, Ph), 5.14 (brs, 1H, H-1'), 5.11 (s, 1H, H-2'), 4.30-4.38 (m, 2H, H-3' and H-4a'), 3.96-4.02 (m, 1H, H-4b'), 3.45 (s, 3H, OMe).
$^{13}$C NMR (75 MHz, CDCl$_3$): δ 166.1 (PhCO), 133.5, 129.8, 129.1, 128.5 (Ph), 106.5 (C-1'), 83.6 (C-2'), 75.2 (C-3'), 73.8 (C-4'), 55.0 (OMe).
HRMS: [M+Ma]$^+$ calculated for C$_{12}$H$_{14}$O$_6$Na, 261.0734; found, 261.0738.

Example 29: 1-O-Methyl-2-O-benzoyl-3-O-diisopropylphosphonomethyl-L-threose (24)

To a solution of 23 (2.23 g, 9.36 mmol) and diisopropylphosphonomethyl trifluoromethanesulfonate (4.61 g, 14.04 mmol) in anhydrous THF (50 mL) was added NaH (60% in mineral oil, 0.45 g, 11.23 mmol) at −5° C. The reaction mixture was warmed to 0° C. and stirred for 15 min. The reaction was quenched with sat. aq. NH$_4$Cl and concentrated.

The residue was partitioned between water and EtOAc. The organic layer was washed with brine, dried over Na$_2$SO$_4$, and concentrated under reduced pressure. The residue was purified by chromatography on a silica gel column (2:1 to 1:1, hexane/EtOAc) to afford 24 (3.43 g, 87% yield) as a colorless oil containing about 10% of β-anomer.
α-Anomer:
$^1$H NMR (300 MHz, CDCl$_3$): δ 8.02-8.05 (m, 2H, Ph), 7.57-7.62 (m, 1H, Ph), 7.43-7.48 (m, 2H, Ph), 5.29 (s, 1H, H-2'), 5.04 (s, 1H, H-1'), 4.69-4.81 [m, 2H, CH(CH$_3$)$_2$], (4.28-4.41) (m, 2H, H-4a' amd H-3'), 3.84-4.15 (m, 3H, H-4b' and PCH$_2$), 3.40 (s, 3H, OMe), 1.31-1.34 [m, 2H, CH(CH$_3$)$_2$].

$^{13}$C NMR (75 MHz, CDCl$_3$): δ 165.5 (PhCO), 133.5, 129.8, 129.3, 128.5 (Ph), 107.0 (C-1'), 84.8 ($^3J_{P,C}$=10.3 Hz, C-3'), 81.0 (C-2'), 71.4, 71.1 [CH(CH$_3$)$_2$], 71.1 (C-4'), 65.0 ($^1J_{P,C}$=167.9 Hz, PCH$_2$), 54.7 (OMe), 24.0 [CH(CH$_3$)$_2$].

$^{31}$P NMR (121 MHz, CDCl$_3$): δ 18.5.

β-anomer:

$^1$H NMR (600 MHz, CDCl$_3$): δ 8.06-8.08 (m, 2H, Ph), 7.58-7.61 (m, 2H, Ph), 7.45-7.48 (m, 2H, Ph), 5.27 (d, J=4.5 Hz, 1H, H-1'), 5.10 (t, J=4.6 Hz, 1H, H-2'), 4.71-4.78 [m, 2H, CH(CH$_3$)$_2$], 4.56-4.58 (m, 1H, H-3'), 4.22 (dd, J=9.9, 6.7 Hz, 1H, H-4a'), 3.89 (dd, J=9.9, 3.6 Hz, 1H, H-4b'), 3.76-3.89 (m, 2H, PCH$_2$), 3.33 (s, 3H, OMe), 1.29-1.34 [m, 2H, CH(CH$_3$)$_2$].

$^{13}$C NMR (125 MHz, CDCl$_3$): δ 165.8 (PhCO), 133.4, 129.8, 129.3, 128.5 (Ph), 101.8 (C-1'), 83.2 ($^3J_{P,C}$=12.5 Hz, C-3'), 79.5 (C-2'), 71.4, 71.3 [CH(CH$_3$)$_2$], 68.5 (C-4'), 64.6 ($^1J_{P,C}$=169.9 Hz, PCH$_2$), 55.4 (OMe), 24.0 [CH(CH$_3$)$_2$].

$^{31}$P NMR (121 MHz, CDCl$_3$): δ 18.1.

HRMS: [M+H]$^+$ calculated for C$_{19}$H$_{30}$O$_8$P, 417.1673; found, 417.1673.

Example 30: 1-O-Acetyl-2-o-benzoyl-3-O-diisopropylphosphonomethyl-L-threose (25)

To a solution of 24 (0.20 g, 0.48 mmol) in anhydrous CH$_2$Cl$_2$ (5 mL) was added acetic anhydride (0.18 mL, 1.92 mmol) and a catalytic amount of sulphuric acid. After stirring overnight at room temperature, the reaction mixture was neutralized by Et$_3$N (3 mL) at 0° C. and concentrated under reduced pressure. The crude product was diluted by EtOAc (20 mL), washed with brine, dried over Na$_2$SO$_4$ and concentrated under reduced pressure. The residue was purified by chromatography on a silica gel column (1:1, hexane/EtOAc) to afford 25 (0.18 g, 83% yield) as a colorless oil and the mixture containing about 10% of the β-anomer. The major α-anomer was characterized as follows.

α-anomer:

$^1$H NMR (600 MHz, CDCl$_3$): δ 8.02-8.04 (m, 2H, Ph), 7.59-7.62 (m, 1H, Ph), 7.45-7.48 (m, 2H, Ph), 6.31 (s, 1H, H-1'), 5.42 (d, J=0.9 Hz, 1H, H-2'), 4.74-4.80 [m, 2H, CH(CH$_3$)$_2$], 4.44 (dd, J=10.1, 6.7 Hz, 1H, H-4a'), 4.30-4.32 (m, 1H, H-3'), 4.12 (dd, J=10.1, 4.3 Hz, 1H, H-4b'), 3.86-4.10 (m, 2H, PCH$_2$), 2.12 (s, 3H, CH$_3$CO), 1.33-1.35 [m, 2H, CH(CH$_3$)$_2$].

$^{13}$C NMR (125 MHz, CDCl$_3$): δ 169.7 (COCH$_3$), 165.3 (PhCO), 133.7, 129.8, 128.9, 128.6 (Ph), 99.8 (C-1'), 84.3 ($^3J_{P,C}$=11.6 Hz, C-3'), 80.3 (C-2'), 73.1 (C-4'), 71.3, 71.2 [CH(CH$_3$)$_2$], 65.2 ($^1J_{P,C}$=168.6 Hz, PCH$_2$), 24.0 [CH(CH$_3$)$_2$], 21.1 (CH$_3$CO).

$^{31}$P NMR (121 MHz, CDCl$_3$): δ 18.2. HRMS: [M+Ma]$^+$ calculated for C$_{20}$H$_{29}$O$_9$PNa, 467.1442; found, 439.1444.

Example 31: 1'α-(N-Benzoylcytosin-1-yl)-2'-O-benzoyl-3'-O-diisopropylphosphono-methyl-L-threose (26)

A suspension of N$^6$-Benzoylcytosine (97 mg, 0.45 mmol) in anhydrous CH$_3$CN (2 mL) was treated with BSA (0.25 mL, 1.01 mmol) and heated to 65° C. After stirring for 1 hour, a solution of 25 (100 mg, 0.23 mmol) in anhydrous CH$_3$CN (1 mL) was added followed by TMSOTf (0.12 mL, 0.68 mmol) at 0° C. The mixture was stirred overnight at 0° C. The reaction mixture was poured into an ice-cold 50 mL of (1:1) sat. aq. NaHCO$_3$:AcOEt. The organic layer was washed with brine, dried over Na$_2$SO$_4$ and concentrated. The residue was purified by column chromatography (50:1, DCM/MeOH) gave 26 (54 mg, 40% yield) as a white foam.

$^1$H NMR (500 MHz, CDCl$_3$): δ 8.72 (brs, 1H, NH), 8.04-8.06 (m, 3H, H-6 and Ph), 7.90 (d, J=7.4 Hz, Ph), 7.59-7.63 (m, 3H, H-5 and Ph), 7.52 (t, J=7.9 Hz, 2H, Ph), 7.47 (t, J=8.1 Hz, 2H, Ph), 6.32 (s, 1H, H-1'), 5.51 (s, 1H, H-2'), 4.70-4.76 [m, 2H, CH(CH$_3$)$_2$], 4.52 (d, J=10.0 Hz, H-4a'), 4.30-4.33 (m, 2H, H-4b' and H-3'), 3.85-3.95 (m, 2H, PCH$_2$), 1.31-1.34 [m, 12H, CH(CH$_3$)$_2$].

$^{13}$C NMR (125 MHz, CDCl$_3$): δ 165.1 (PhCO), 162.4 (C-4), 155.0 (C-2), 145.1 (C-6), 133.7, 133.2, 129.9, 129.0, 128.8, 128.5, 127.5 (Ph), 96.2 (C-5), 90.9 (C-1'), 83.3 ($^3J_{P,C}$=9.6 Hz, C-3'), 79.6 (C-2'), 74.5 (C-4'), 73.9 (C-3'), 71.3 [CH(CH$_3$)$_2$], 64.6 ($^1J_{P,C}$=168.5 Hz, PCH$_2$), 24.0 [CH(CH$_3$)$_2$]. $^{31}$P NMR (121 MHz, CDCl$_3$): δ 17.9.

HRMS: [M+H]$^+$ calculated for C$_{29}$H$_{35}$N$_3$O$_9$P, 600.2105; found, 600.2130.

Example 32: 1'α-(N$^6$-Benzoylcytosin-1-yl)-3'-O-diisopropylphosphonomethyl-L-threose (27).

This compound was prepared as described for 10, 80% yield.

$^1$H NMR (500 MHz, CDCl$_3$): δ 9.31 (brs, 1H, NH), 8.02 (d, J=7.5 Hz, 1H, H-6), 7.93-7.95 (m, 2H, Ph), 7.57-7.60 (m, 3H, H-5 and Ph), 7.49 (t, J=8.0 Hz, 2H, Ph), 5.87 (s, 1H, H-1'), 5.52 (brs, 1H, OH), 4.64-4.72 [m, 2H, CH(CH$_3$)$_2$], 4.52 (s, 1H, H-2'), 4.34-4.39 (m, 2H, H-4'), 4.18 (s, 1H, H-3'), 3.73-3.87 (m, 2H, PCH$_2$), 1.26-1.30 [m, 12H, CH(CH$_3$)$_2$].

$^{13}$C NMR (125 MHz, CDCl$_3$): δ 166.7 (PhCO), 162.7 (C-4), 155.8 (C-2), 144.8 (C-6), 133.1, 132.9, 128.8, 127.8) (Ph), 96.3 (C-5), 94.6 (C-1'), 85.5 ($^3J_{P,C}$=10.4 Hz, C-3'), 78.7 (C-2'), 74.0 (C-4'), 71.2 [CH(CH$_3$)$_2$], 64.2 ($^1J_{P,C}$=168.8 Hz, PCH$_2$), 23.9 [CH(CH$_3$)$_2$].

$^{31}$P NMR (121 MHz, CDCl$_3$): δ 18.5.

HRMS: [M+H]$^+$ calculated for C$_{22}$H$_{31}$N$_3$O$_8$P, 496.1843; found, 496.1856.

Example 33: 1'α-(N$^6$-Benzoylcytosin-1-yl)-2'-deoxy-3'-O-diisopropylphosphonomethyl-L-threose (28)

This compound was prepared as described for 12, 70% yield.

$^1$H NMR (300 MHz, CDCl$_3$): δ 8.63 (brs, 1H, NH), 8.09 (d, J=7.2 Hz, 1H, H-6), 7.91 (d, J=7.6 Hz, 2H, Ph), 7.60-7.66 (m, 1H, Ph), 7.51-7.56 (m, 3H, H-5 and Ph), 6.21 (dd, J=7.1 Hz, 1.8 Hz, 1H, H-1'), 4.66-4.79 [m, 2H, CH(CH$_3$)$_2$], 4.49 (dd, J=10.5, 1.2 Hz, 1H, H-4a'), 4.39 (t, J=4.0 Hz, 1H, H-3'), 4.06 (dd, J=10.5, 3.5 Hz, 1H, H-4b'), 3.57-3.70 (m, 2H, PCH$_2$), 2.52-2.61 (m, 1H, H-2a'), 2.46 (d, J=15.2 Hz, 1H, H-2b'), 1.28-1.36 [m, 12H, CH(CH$_3$)$_2$].

$^{13}$C NMR (75 MHz, CDCl$_3$): δ 166.1 (PhCO), 162.1 (C-4), 155.4 (C-2), 145.3 (C-6), 133.1, 129.1, 127.4 (Ph), 95.6 (C-5), 87.8 (C-1'), 80.2 ($^3J_{P,C}$=9.7 Hz, C-3'), 75.1 (C-4'), 71.2 [CH(CH$_3$)$_2$], 63.8 ($^1J_{P,C}$=169.2 Hz, PCH$_2$), 38.7 (C-2'), 24.0 [CH(CH$_3$)$_2$].

$^{31}$P NMR (121 MHz, CDCl$_3$): δ 18.3.

HRMS: [M+H]$^+$ calculated for C$_{22}$H$_{31}$N$_3$O$_7$P, 480.1894; found, 480.1889.

Example 34: 1'α-(Cytosin-1-yl)-2'-deoxy-3'-O-diisopropylphosphonomethyl-L-threose (29)

This compound was prepared as described for 14, 88% yield.

$^1$H NMR (300 MHz, CDCl$_3$): δ 7.68 (d, J=7.4 Hz, 1H, H-6), 6.19 (dd, J=7.4, 1.9 Hz, 1H, H-1'), 5.78 (d, J=7.5 Hz,

1H, H-5), 4.61-4.76 [m, 2H, CH(CH$_3$)$_2$], 4.35 (dd, J=10.4, 1.3 Hz, 1H, H-4a'), 4.27-4.30 (m, 1H, H-3'), 3.93 (dd, J=10.4, 3.6 Hz, 1H, H-4b'), 3.63 (d, J=9.2 Hz, 2H, PCH$_2$), 2.44-2.54 (m, 1H, H-2a'), 2.89 (d, J=15.1 Hz, 1H, H-2b'), 1.26-1.33 [m, 12H, CH(CH$_3$)$_2$].

$^{13}$C NMR (75 MHz, CDCl$_3$): δ 165.8 (C-4), 156.1 (C-2), 141.7 (C-6), 93.6 (C-5), 86.6 (C-1'), 80.3 ($^3$J$_{P,C}$=11.6 Hz, C-3'), 74.1 (C-4'), (71.3, 71.1) [CH(CH$_3$)$_2$], 63.7 ($^1$J$_{P,C}$=170.2 Hz, PCH$_2$), 38.6 (C-2'), 24.0 [CH(CH$_3$)$_2$].

$^{31}$P NMR (121 MHz, CDCl$_3$): δ 18.4.

HRMS: [M+H]$^+$ calculated for C$_{15}$H$_{27}$N$_3$O$_6$P, 376.1632; found, 376.1629.

Example 35: 1'α-(Cytosin-1-yl)-2'-deoxy-3'-O-phosphonomethyl-L-threose (30)

This compound was prepared as described for 16, 48% yield.

$^1$H NMR (600 MHz, D$_2$O): δ 7.95 (d, J=7.5 Hz, 1H, H-6), 6.19 (dd, J=8.0, 2.0 Hz, 1H, H-1'), 6.04 (d, J=7.6 Hz, 1H, H-5), 4.40 (d, J=10.2 Hz, 1H, H-4a'), 4.36-4.38 (m, 1H, H-3'), 3.95 (dd, J=10.4, 3.6 Hz, 1H, H-4b'), 3.45-3.52 (m, 2H, PCH$_2$), 2.52-2.58 (m, 1H, H-2a'), 2.46 (d, J=15.4 Hz, 1H, H-2b').

$^{13}$C NMR (150 MHz, D$_2$O): δ 165.8 (C-4), 157.3 (C-2), 142.4 (C-6), 95.6 (C-5), 85.9 (C-1'), 79.2 ($^3$J$_{P,C}$=11.6 Hz, C-3'), 73.6 (C-4'), 64.9 ($^1$J$_{P,C}$=155.3 Hz, PCH$_2$), 36.6 (C-2').

$^{31}$P NMR (121 MHz, D$_2$O): δ 14.6.

HRMS: [M−H]$^-$ calculated for C$_9$H$_{13}$N$_3$O$_6$P, 290.0547; found, 290.0545.

Example 36: 1'α-(Cytosin-1-yl)-2'-deoxy-3'-O-{[N,N'-bis(n-propyl-L-alaninate)]methyl-phosphonobisamidate}-L-threose (PMDTC bis-Ala-i-propyl ester; compound 31)

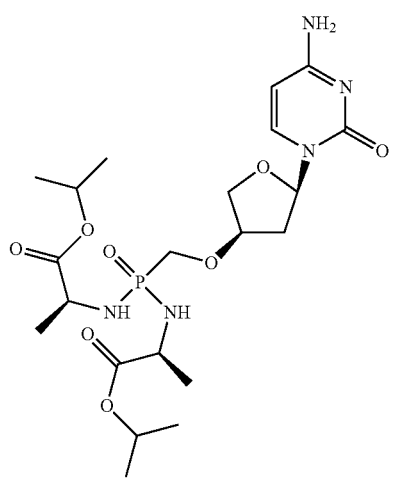 [SMILES: CC(C)OC(=O)[C@H](C)NP(=O)(CO[C@H]1CO[C@@H](n2ccc(N)nc2=O)C1)N[C@@H](C)C(=O)OC(C)C]

This compound was prepared as described for 17, 26% yield.

$^1$H NMR (600 MHz, CD$_3$OD): δ 7.84 (d, J=7.4 Hz, 1H, H-6), 6.09 (d, J=6.6 Hz, 1H, H-1'), 5.90 (d, J=7.4 Hz, 1H, H-5), 4.96-5.02 [m, 2H, CH(CH$_3$)$_2$], 4.41 (d, J=10.3 Hz, 1H, H-4a'), 4.25-4.28 (m, 1H, H-3'), 3.84-3.95 (m, 3H, H-4b' and Ala-CH), 3.61-3.75 (m, 2H, PCH$_2$), 2.48-2.55 (m, 1H, H-2a'), 2.19 (d, J=15.0 Hz, 1H, H-2b'), 1.33-1.36 (m, 6H, Ala-CH$_3$), 1.23-1.26 [m, 12H, CH(CH$_3$)$_2$].

$^{13}$C NMR (150 MHz, CD$_3$OD): δ 175.3, 175.2 (Ala-CO), 167.7 (C-4), 158.4 (C-2), 143.3 (C-6), 95.6 (C-5), 88.1 (C-1'), 82.3 ($^3$J$_{P,C}$=13.4 Hz, C-3'), 75.0 (C-4'), 70.2 [CH(CH$_3$)$_2$], 66.8 ($^1$J$_{P,C}$=137.0 Hz, PCH$_2$), 50.2, 49.9 (Ala-CH), 39.8 (C-2'), 22.0 [CH(CH$_3$)$_2$], 21.4, 21.2 (Ala-CH$_3$).

$^{31}$P NMR (121 MHz, CD$_3$OD): δ 23.1.

HRMS: [M+H]$^+$ calculated for C$_{21}$H$_{37}$N$_5$O$_8$P, 518.2374; found, 518.2385.

Example 37: 1'α-(Cytosin-1-yl)-2'-deoxy-3'-O-{[N-(isopropyl-L-alaninate)](phenoxy)-methyl-phosphonoamidate}-L-threose (PMDTC Ala-isopropyl, OPh ester; compound 32)

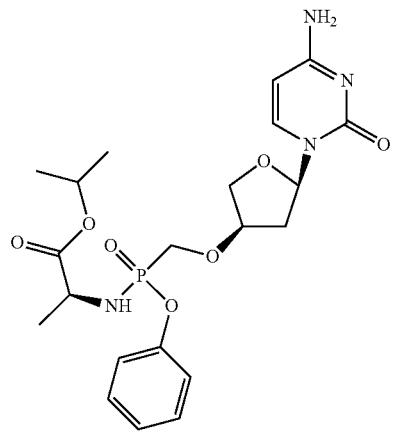 [SMILES: CC(C)OC(=O)[C@H](C)NP(=O)(CO[C@H]1CO[C@@H](n2ccc(N)nc2=O)C1)Oc1ccccc1]

This compound was prepared as described for 18, 15% yield.

$^1$H NMR (300 MHz, CD$_3$OD): δ (7.83, 7.79) (d, J=7.5 Hz, 1H, H-6), 7.32-7.38 (m, 2H, Ph), 7.14-7.21 (m, 3H, Ph), 6.07-6.12 (m, 1H, H-1'), (5.80, 5.79) (d, J=7.5 Hz, 1H, H-5), 4.85-4.99 [m, 1H, CH(CH$_3$)$_2$], 4.38-4.44 (m, 1H, H-4a'), 4.27-4.35 (m, 1H, H-3'), 3.80-3.99 (m, 4H, H-4b', PCH$_2$ and Ala-CH), 2.48-2.58 (m, 1H, H-2a'), 2.19-2.24 (m, 1H, H-2b'), 1.18-1.29 [m, 9H, Ala-CH$_3$ and CH(CH$_3$)$_2$]. $^{31}$P NMR (121 MHz, CD$_3$OD): δ 23.9, 22.7.

HRMS: [M+H]$^+$ calculated for C$_{21}$H$_{30}$N$_4$O$_7$P, 481.1846; found, 481.1848.

Example 38: 1'α-(2-Amino-6-chloropurin-9-yl)-2'-O-benzoyl-3'-O-tert-butyldimethylsilyl-L-threose (33)

To a solution of 3 (0.35 g, 0.92 mmol), 2-amino-6-chloro-9H-purine (0.17 g, 1.01 mmol), and DBU (0.41 mL, 2.76 mmol) in dry MeCN (9 mL) was added TMSOTf (0.66 mL, 3.68 mmol) at 0° C. The resulting clear brown solution was stirred 1.5 hour at 70° C., after which it was cooled to room temperature and aq. sat. NaHCO$_3$ (20 mL) was added. The aqueous phase was extracted with EtOAc (3×10 mL), dried over Na$_2$SO$_4$, filtered, and evaporated under reduced pressure. The residue was purified by column chromatography on silica gel (10:1 to 5:1, hexane/EtOAc) to afford the desired product 33 (0.30 g, 67%) as a white foam.

$^1$H NMR (300 MHz, CDCl$_3$): δ 8.22 (s, 1H, H-8), 8.03 (d, J=7.2 Hz, 2H, Ph), 7.60 (t, J=7.3 Hz, 1H, Ph), 7.45 (t, J=7.5 Hz, 2H, Ph), 6.29 (s, 1H, H-1'), 5.54 (s, 1H, H-2'), 5.50 (brs, 2H, NH$_2$), 4.52 (s, 1H, H-3'), 4.33 (dd, J=9.8, 3.7 Hz, 1H, H-4a'), 4.25 (d, J=9.8 Hz, 1H, H-4b'). 0.88 (s, 9H, TBS), 0.15 (s, 3H, TBS), 0.11 (s, 3H, TBS).

$^{13}$C NMR (75 MHz, CDCl$_3$): δ 164.9 (PhCO), 159.1 (C-2), 153.2 (C-4), 151.0 (C-6), 141.0 (C-8), 133.7, 129.7, 128.6, 128.5 (Ph), 125.0 (C-5), 87.7 (C-1'), 82.5 (C-2'), 76.5 (C-4'), 75.1 (C-3'), 25.5 (TBS), 17.8 (TBS), −5.0 (TBS), −5.3 (TBS).

HRMS: [M+H]$^+$ calculated for C$_{22}$H$_{29}$ClN$_5$O$_4$Si, 490.1672; found, 490.1681.

Example 39: 1'α-(2-Amino-6-chloropurin-9-yl)-2'-O-benzoyl-L-threose (34)

This compound was prepared as described for 6, 97% yield.

$^1$H NMR (300 MHz, CDCl$_3$): δ 7.98 (s, 1H, H-8), 8.01 (d, J=7.2 Hz, 2H, Ph), 7.63 (t, J=7.3 Hz, 1H, Ph), 7.47 (t, J=7.5 Hz, 2H, Ph), 5.92 (d, J=1.7 Hz, 1H, H-1'), 5.58 (s, 1H, H-2'), 5.42 (brs, 2H, NH$_2$), 4.57 (d, J=3.2 Hz, 1H, H-3'), 4.33 (d, J=9.8 Hz, 1H, H-4a'), 4.22 (dd, J=9.8, 3.7 Hz, 1H, H-4b').

$^{13}$C NMR (75 MHz, CDCl$_3$): δ 165.7 (PhCO), 158.4 (C-2), 152.5 (C-4), 151.9 (C-6), 142.1 (C-8), 134.0, 129.8, 128.6, 128.4 (Ph), 126.0 (C-5), 90.4 (C-1'), 83.8 (C-2'), 75.8 (C-4'), 74.6 (C-3').

HRMS: [M+H]$^+$ calculated for C$_{16}$H$_{15}$ClN$_5$O$_4$, 376.0807; found, 376.0808.

Example 40: 1'α-(2-Amino-6-chloropurin-9-yl)-2'-O-benzoyl-3'-O-diisopropyl-phosphonomethyl L-threose (35)

This compound was prepared as described for 24, 67% yield.

$^1$H NMR (300 MHz, CDCl$_3$): δ 8.12 (s, 1H, H-8), 8.05 (d, J=7.2 Hz, 2H, Ph), 7.64 (t, J=7.4 Hz, 1H, Ph), 7.47 (t, J=7.9 Hz, 2H, Ph), 6.22 (d, J=1.3 Hz, 1H, H-1'), 5.85 (s, 1H, H-2'), 5.33 (brs, 2H, NH$_2$), 4.71-4.82 [m, 2H, CH(CH$_3$)$_2$], 4.42-4.45 (m, 2H, H-3' and H-4a'), 4.33 (dd, J=10.7, 4.7 Hz, 1H, H-4b'), 3.86-4.06 (m, 2H, PCH$_2$), 1.30-1.37 [m, 12H, CH(CH$_3$)$_2$].

$^{13}$C NMR (75 MHz, CDCl$_3$): δ 165.1 (PhCO), 159.2 (C-2), 153.4 (C-4), 151.4 (C-6), 141.1 (C-8), 134.0, 129.9, 128.7, 128.6 (Ph), 125.3 (C-5), 88.2 (C-1'), 84.1 ($^3$J$_{P,C}$=10.6 Hz, C-3'), 79.8 (C-2'), 73.3 (C-4'), 71.5 [CH(CH$_3$)$_2$], 64.7 ($^1$J$_{P,C}$=168.5 Hz, PCH$_2$). 23.9 [CH(CH$_3$)$_2$].

$^{31}$P NMR (121 MHz, CDCl$_3$): δ 17.8.

HRMS: [M+H]$^+$ calculated for C$_{23}$H$_{30}$ClN$_5$O$_7$P, 554.1566; found, 554.1568.

Example 41: 1'α-(2-Amino-6-chloropurin-9-yl)-3'-O-diisopropylphosphonomethyl L-threose (36)

A solution of 35 (5.0 g, 9.03 mmol) in 2 M ammonia in MeOH (150 mL) was stirred at room temperature for 2 hours. The mixture was concentrated and the residue was purified by column chromatography (20:1, CH$_2$Cl$_2$/MeOH) to give compound 36 (3.0 g, 75% yield) as a white foam. $^1$H NMR (300 MHz, CDCl$_3$): δ 8.02 (s, 1H, H-8), 5.91 (d, J=2.7 Hz, 1H, H-1'), 5.72 (brs, 3H, NH$_2$ and OH), 4.76 (s, 1H, H-2'), 4.62-4.73 [m, 2H, CH(CH$_3$)$_2$], 4.25-4.29 (m, 3H, H-3' and H-4'), 3.76-3.91 (m, 2H, PCH$_2$), 1.26-1.33 [m, 12H, CH(CH$_3$)$_2$].

$^{13}$C NMR (75 MHz, CDCl$_3$): δ 159.2 (C-2), 153.2 (C-4), 151.1 (C-6), 141.1 (C-8), 125.0 (C-5), 90.4 (C-1'), 86.4 ($^3$J$_{P,C}$=8.9 Hz, C-3'), 78.9 (C-2'), 72.3 (C-4'), 71.8 [CH(CH$_3$)$_2$], 64.8 ($^1$J$_{P,C}$=167.8 Hz, PCH$_2$). 23.9 [CH(CH$_3$)$_2$].

$^{31}$P NMR (121 MHz, CDCl$_3$): δ 18.6.

HRMS: [M+H]$^+$ calculated for C$_{16}$H$_{26}$ClN$_5$O$_6$P, 450.1304; found, 450.1301.

Example 42: 1'α-(2-Amino-6-chloropurin-9-yl)-2'-deoxy-3'-O-diisopropyl-phosphono-methyl L-threose (37)

This compound was prepared as described for 12, 68% yield.

$^1$H NMR (300 MHz, CDCl$_3$): δ 8.20 (s, 1H, H-8), 6.30 (dd, J=6.8, 3.1 Hz, 1H, H-1'), 5.30 (brs, 2H, NH$_2$), 4.65-4.83 [m, 2H, CH(CH$_3$)$_2$], 4.50 (brs, 1H, H-3'), 4.33 (d, J=10.5 Hz, 1H, H-4a'), 4.04 (dd, J=10.4, 4.2 Hz, 1H, H-4b'). 3.67-3.80 (m, 2H, PCH$_2$), 2.56-2.70 (m, 2H, H-2'), 1.29-1.36 [m, 12H, CH(CH$_3$)$_2$].

$^{13}$C NMR (75 MHz, CDCl$_3$): δ 158.7 (C-2), 153.2 (C-4), 151.1 (C-6), 141.0 (C-8), 125.1 (C-5), 83.1 (C-1'), 80.0 ($^3$J$_{P,C}$=10.0 Hz, C-3'), 73.4 (C-4'), 71.1 [CH(CH$_3$)$_2$], 63.8 ($^1$J$_{P,C}$=167.8 Hz, PCH$_2$), 37.8 (C-2'), 23.7 [CH(CH$_3$)$_2$].

$^{31}$P NMR (121 MHz, CDCl$_3$): δ 18.1.

HRMS: [M+H]$^+$ calculated for C$_{16}$H$_{26}$ClN$_5$O$_5$P, 434.1354; found, 434.1354.

Example 43: 1'α-(Guanin-9-yl)-2'-deoxy-3'-O-phosphonomethyl L-threose (38)

To a solution of 37 (184 mg, 0.42 mmol) in anhydrous CH$_3$CN (9 mL) was added 2,6-lutidine (0.40 mL, 3.39 mmol) and trimethylsilyl bromide (0.45 mL, 3.39 mmol) at room temperature. After stirring overnight at room temperature, the solvent was removed under reduced pressure and co-evaporated three times with anhydrous methanol (3×3 mL). The residue was dissolved in anhydrous MeOH (4 mL), and 2-mercaptoethanol (0.15 mL, 2.12 mmol) and NaOMe (5.4 M in MeOH, 0.39 mL, 2.12 mmol) was added. The mixture was refluxed for 19 hours, cooled, quenched with 2 mL TEAB buffer and evaporated. The residue was partitioned between water and EtOAc, and the aqueous phase was lyophilized and the residue was purified by RP-HPLC running a gradient of CH$_3$CN in 0.1 M TEAB buffer solution from 0% to 30% to afford 38 (90 mg, 49%) as a yellowish solid.

$^1$H NMR (300 MHz, D$_2$O): δ 8.05 (s, 1H, H-8), 6.06 (dd, J=7.9, 2.0 Hz, 1H, H-1'), 4.39 (brs, 1H, H-3'), 4.23 (d, J=10.4 Hz, 1H, H-4a'), 3.94 (dd, J=10.4, 4.0 Hz, 1H, H-4b'). 3.55 (d, J=9.3 Hz, 2H, PCH$_2$), 2.60-2.70 (m, 1H, H-2a'), 2.49 (d, J=15.4 Hz, H-2b').

$^{13}$C NMR (75 MHz, D$_2$O): δ 158.3 (C-6), 153.4 (C-2), 150.7 (C-4), 138.1 (C-8), 115.4 (C-5), 82.8 (C-1'), 79.6 ($^3$J$_{P,C}$=12.0 Hz, C-3'), 73.2 (C-4'), 65.2 ($^1$J$_{P,C}$=155.2 Hz, PCH$_2$), 36.6 (C-2'). $^{31}$P NMR (121 MHz, D$_2$O): δ 15.1.

HRMS: [M−H]$^−$ calculated for C$_{10}$H$_{13}$N$_5$O$_6$P, 330.0609; found, 330.0604.

Example 44: 1'α-(Guanin-9-yl)-2'-deoxy-3'-O—[N, N'-bis(n-propyl-L-phenylalaninate)]-methylphosphonobisamidate]-L-threose (PMDTG bis-Phe-n-propyl ester; compound 39)

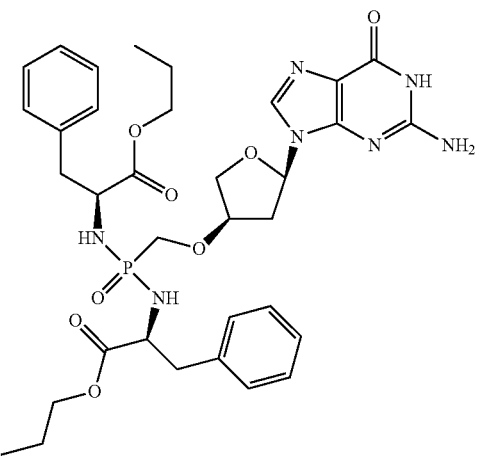 [SMILES: CCCOC(=O)[C@H](Cc1ccccc1)NP(=O)(CO[C@H]1CO[C@@H](n2cnc3c(=O)[nH]c(N)nc32)C1)N[C@@H](Cc1ccccc1)C(=O)OCCC]

This compound was prepared as described for 17 in 24% yield.

$^1$H NMR (300 MHz, DMSO-d$_6$): δ 10.59 (brs, 1H, NH), 7.86 (s, 1H, H-8), 7.12-7.28 (m, 10H, Ph), 6.47 (brs, 2H, NH$_2$), 6.04 (dd, J=8.1, 2.3 Hz, 1H, H-1'), 4.54 (t, J=11.3 Hz, 1H, NH), 4.21 (t, J=11.3 Hz, 1H, NH), 3.87-4.17 (m, 8H, H-3', H4a', CH$_2$CH$_2$CH$_3$ and PCH$_2$), 3.79 (dd, J=10.2, 4.0 Hz, 1H, H-4b'), 3.13-3.37 (m, 2H, Phe-CH), 2.75-2.94 (m, 4H, Phe-CH$_2$), 2.55-2.65 (m, 1H, H-2a'), 2.20 (d, J=14.4 Hz, H-2b'), 1.40-1.57 (m, 4H, CH$_2$CH$_2$CH$_3$), 0.74-0.84 (m, 6H, CH$_2$CH$_2$CH$_3$).

$^{31}$P NMR (121 MHz, DMSO-d$_6$): δ20.3.

HRMS: [M+H]$^+$ calculated for C$_{34}$H$_{45}$N$_7$O$_8$P, 710.3062; found, 710.3063.

Example 45: 1'α-(Guanin-9-yl)-2'-deoxy-3'-O—[N, N'-bis(n-propyl-L-alaninate)]methyl-phosphonobisamidate]-L-threose (PMDTG bis-Ala-i-propyl ester; compound 40)

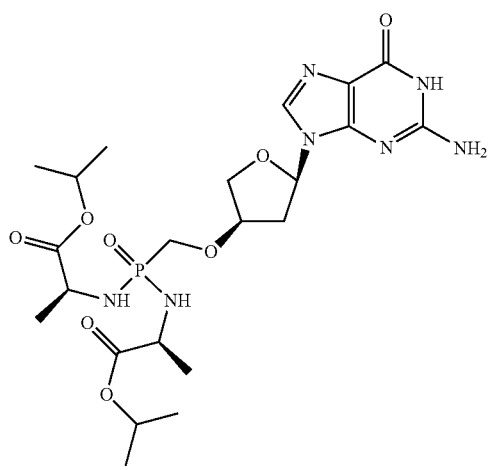 [SMILES: CC(C)OC(=O)[C@H](C)NP(=O)(CO[C@H]1CO[C@@H](n2cnc3c(=O)[nH]c(N)nc32)C1)N[C@@H](C)C(=O)OC(C)C]

This compound was prepared as described for 17 in 23% yield.

$^1$H NMR (300 MHz, DMSO-d$_6$): δ (7.86) (s, 1H, H-8), 6.59 (brs, 2H, NH$_2$), 6.05 (dd, J=8.1, 2.5 Hz, 1H, H-1'), 4.84-4.92 [m, 2H, CH(CH$_3$)$_2$], 4.42-4.59 (m, 2H, NH), 4.35 (brs, 1H, H-3'), 4.18 (d, J=9.8 Hz, H-4a'), 3.75-3.90 (m, 3H, H-4b' and Ala-CH), 3.56-3.72 (m, 2H, PCH$_2$), 2.59-2.69 (m, 1H, H-2a'), 2.30 (d, J=14.7 Hz, H-2b'), 1.27 (t, J=7.5 Hz, 6H, Ala-CH$_3$), 1.17-1.19 [m, 12H, CH(CH$_3$)$_2$].

$^{31}$P NMR (121 MHz, DMSO-d$_6$): δ20.3.

HRMS: [M+H]$^+$ calculated for C$_{22}$H$_{37}$N$_7$O$_8$P, 558.2436; found, 558.2448.

Example 46: 1'α-(Guanin-9-yl)-2'-deoxy-3'-O—{ [N-(isopropyl-L-alaninate)](phenoxy)-methylphosphonoamidate}-L-threose (PMDTG Ala-isopropyl, OPh ester; compound 41)

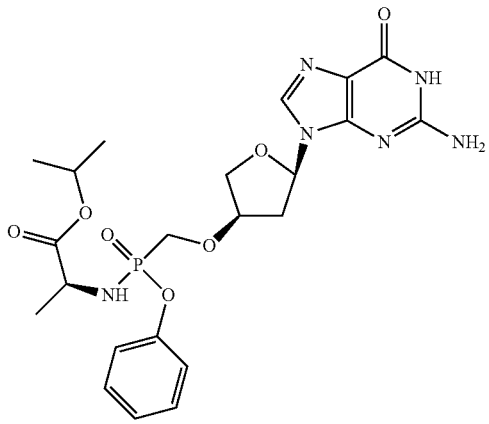 [SMILES: CC(C)OC(=O)[C@H](C)NP(=O)(CO[C@H]1CO[C@@H](n2cnc3c(=O)[nH]c(N)nc32)C1)Oc1ccccc1]

This compound was prepared as described for 18 in 13% yield.

$^1$H NMR (300 MHz, DMSO-d$_6$): δ 7.90, 7.88 (s, 1H, H-8), 7.15-7.40 (m, 5H, Ph), 6.57 (brs, 2H, NH$_2$), 6.07-6.10 (m, 1H, H-1'), 5.62-5.79 (m, 1H, NH), 4.79-4.88 [m, 1H, CH(CH$_3$)$_2$], 4.36-4.45 (m, 1H, H-3'), 4.16-4.22 (m, 1H, H-4a'), 3.83-4.00 (m, 4H, H-4b', PCH$_2$ and Ala-CH), 2.63-2.73 (m, 1H, H-2a'), 2.30-2.42 (m, 1H, H-2b'), 1.12-1.19 [m, 9H, CH(CH$_3$)$_2$ and Ala-CH$_3$]. $^{31}$P NMR (121 MHz, DMSO-d$_6$): δ22.6, 21.9.

HRMS: [M+H]$^+$ calculated for C$_{22}$H$_{30}$N$_6$O$_7$P, 521.1908; found, 521.1914.

Example 47: HBV Antiviral Assay in HepG2 2.2.15 Cells: Primary Assay

The primary anti-HBV assay is performed as previously described (Korba, B F and Milman, G. A cell culture assay for compound which inhibit hepatitis B virus replication. *Antiviral Res.* 1991, 15, 217-228; and Korba, B F and Gerin, J L. Use of a standardized cell culture assay to assess activities of nucleoside analogs again hepatitis B virus replication. *Antiviral Res.* 1992, 19, 55-70) with modifications to use real-time qPCR (TaqMan) to measure extracellular HBV DNA copy number associated with virions released from HepG2 2.2.15 cells. The HepG2 2.2.15 cell line is a stable human hepatoblastoma cell line that contains two copies of the HBV wild-type strain ayw1 genome and constitutively produces high levels of HBV. Antiviral compounds blocking any late step of viral replication such as transcription, translation, pregenome encapsidation, reverse transcription, particle assembly and release can be identified and characterized using this cell line.

Briefly, HepG2 2.2.15 cells are plated in 96-well microtiter plates at $1.5 \times 10^4$ cells/well in Dulbecco's Modified Eagle's Medium supplemented with 2% FBS, 380 μg/mL G418, 2.0 mM L-Glutamine, 100 units/mL Penicillin, 100 μg/mL Streptomycin, and 0.1 mM non-essential amino acids. Only the interior wells are utilized to reduce "edge effects" observed during cell culture; the exterior wells are filled with complete medium to help minimize sample evaporation. After 16-24 hours the confluent monolayer of HepG2 2.2.15 cells is washed and the medium is replaced with complete medium containing various concentrations of a test compound in triplicate Lamivudine (3TC) is used as the positive control, while media alone is added to cells as a negative control (virus control, VC). Three days later the culture medium is replaced with fresh medium containing the appropriately diluted test compounds. Six days following the initial administration of the test compound, the cell culture supernatant is collected, treated with pronase and then used in a real-time quantitative TaqMan qPCR assay. The PCR-amplified HBV DNA is detected in real-time by monitoring increases in fluorescent signal that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($EC_{50}$ & $EC_{90}$ values determined). A tetrazolium dye (MTS; 3-(4,5-dimethylthiazol-2-yl)-5-(3-carboxymethoxyphenyl)-2-(4-sulfophenyl)-2H-tetrazolium; CellTiter®96 Reagent, Promega) uptake assay is then employed to measure cell viability, which is used to calculate toxicity ($CC_{50}$). The Selectivity Index ($SI_{50}$) is calculated as $CC_{50}/IC_{50}$. The data are shown in Table 1.

TABLE 1

| Compound | $EC_{50}$ (μM) | $EC_{90}$ (μM) | $CC_{50}$ (μM) |
|---|---|---|---|
| 3TC (Lamivudine) | 0.03 | >2 | >2 |
| 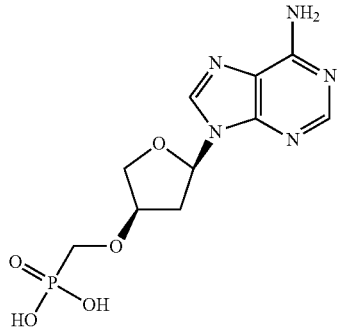 [SMILES: Nc1ncnc2c1ncn2[C@H]1C[C@@H](OCP(=O)(O)O)CO1] | 0.5 | >100 | >100 |
| 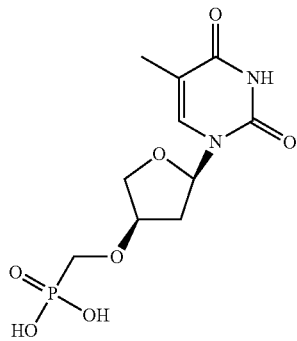 [SMILES: Cc1cn([C@H]2C[C@@H](OCP(=O)(O)O)CO2)c(=O)[nH]c1=O] | 40.2 | >100 | >100 |

TABLE 1-continued
| Compound | EC$_{50}$ (μM) | EC$_{90}$ (μM) | CC$_{50}$ (μM) |
|---|---|---|---|
| 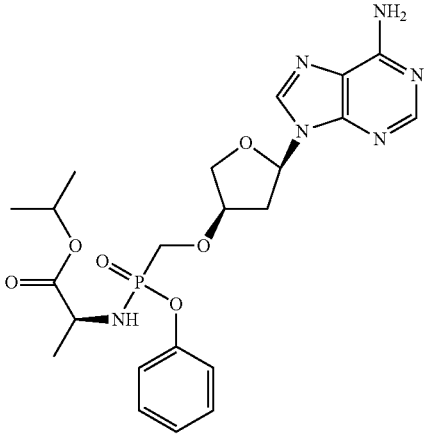 [SMILES: CC(C)OC(=O)[C@H](C)NP(=O)(CO[C@H]1CO[C@@H](n2cnc3c(N)ncnc32)C1)Oc1ccccc1] | 0.03 | >10 | >10 |
| 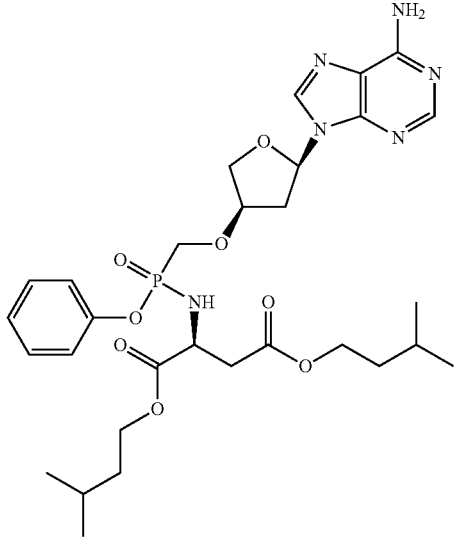 [SMILES: CC(C)CCOC(=O)C[C@H](NP(=O)(CO[C@H]1CO[C@@H](n2cnc3c(N)ncnc32)C1)Oc1ccccc1)C(=O)OCCC(C)C] | 0.01 | 0.98 | 55.47 |
| 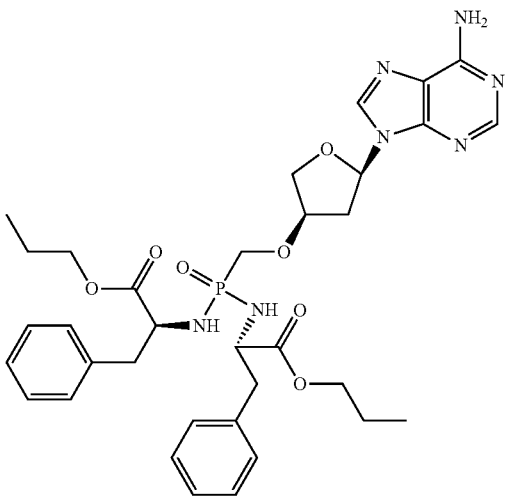 [SMILES: CCCOC(=O)[C@H](Cc1ccccc1)NP(=O)(CO[C@H]1CO[C@@H](n2cnc3c(N)ncnc32)C1)N[C@@H](Cc1ccccc1)C(=O)OCCC] | 0.01 | 4.2 | >100 |

TABLE 1-continued

| Compound | EC$_{50}$ (µM) | EC$_{90}$ (µM) | CC$_{50}$ (µM) |
|---|---|---|---|
| [structure] | 0.26 | >10 | >100 |
| [structure] | 0.25 | >10 | 59.61 |
| [structure] | 0.28 | >10 | >100 |

TABLE 1-continued

| Compound | EC$_{50}$ (μM) | EC$_{90}$ (μM) | CC$_{50}$ (μM) |
|---|---|---|---|
| *(structure)* | >100 | >100 | >100 |
| *(structure)* | 47.89 | >100 | >100 |
| *(structure)* | >100 | >100 | >100 |

TABLE 1-continued

| Compound | EC$_{50}$ (μM) | EC$_{90}$ (μM) | CC$_{50}$ (μM) |
|---|---|---|---|
| | >100 | >100 | >100 |

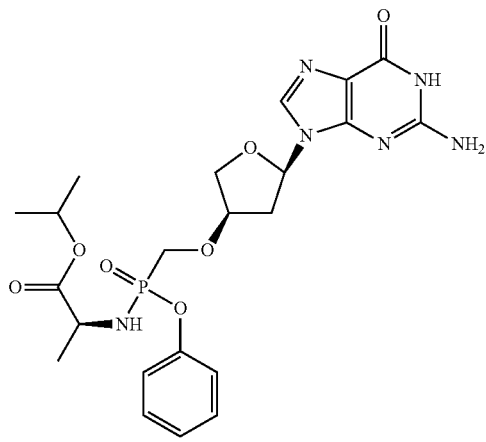 [SMILES: CC(C)OC(=O)[C@H](C)NP(=O)(CO[C@H]1CO[C@@H](n2cnc3c(=O)[nH]c(N)nc32)C1)Oc1ccccc1]

| | >100 | >100 | >100 |
|---|---|---|---|

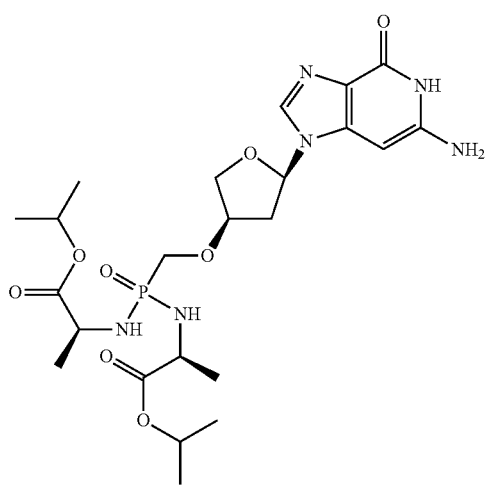 [SMILES: CC(C)OC(=O)[C@H](C)NP(=O)(CO[C@H]1CO[C@@H](n2cnc3c(=O)[nH]c(N)cc32)C1)N[C@@H](C)C(=O)OC(C)C]

Example 48: HBV Antiviral Assay in HepG2 2.2.15 Cells: Secondary Assay

The secondary anti-HBV assay is performed in a manner similar to the primary assay described above in Example 47. However, at the end of the assay, the cells are processed to isolate total intracellular DNA using the Qiagen DNeasy Blood and Tissue kit following the manufacturer's protocol. The real-time TaqMan qPCR assay is then performed using the isolated DNA to measure reductions in intracellular HBV DNA copy number. The results from the secondary assay are used to determine if reductions in extracellular HBV DNA copy number observed in the primary assay correlate to a concomitant reduction in intracellular HBV DNA copy number. Two compounds were tested in this secondary assay and their results are shown in Table 2.

TABLE 2
| Compound | EC$_{50}$ (µM) | EC$_{90}$ (µM) | CC$_{50}$ (µM) |
| --- | --- | --- | --- |
| 3TC (Lamivudine) | <0.01 | >2 | >2 |
| | <0.01 | 0.36 | 35.24 |
| 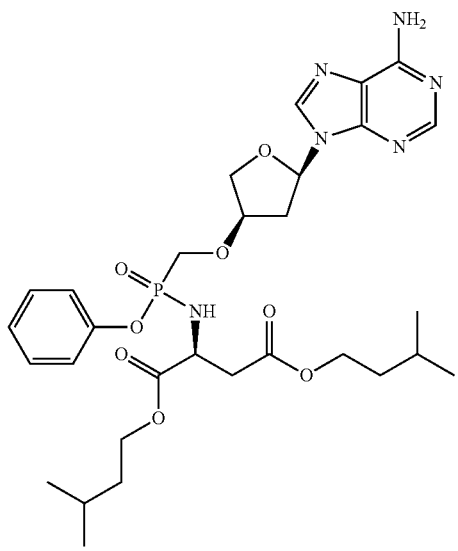 [SMILES: CC(C)CCOC(=O)C[C@H](NP(=O)(CO[C@H]1CO[C@@H](n2cnc3c(N)ncnc32)C1)Oc1ccccc1)C(=O)OCCC(C)C] | 0.03 | 6.37 | >100 |
The invention claimed is:
1. A compound of formula I:
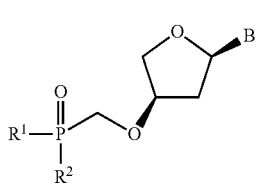
I
wherein
B is any natural nucleobase
R$^1$ has the general formula II
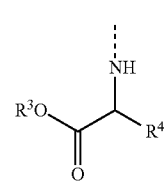
II wherein
R³ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

R⁴ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl, X—COOR⁵, X—O(C=O)—R⁵;

wherein X is aryl, heteroaryl, $C_1$-$C_{10}$ alkyl, $C_2$-$C_{10}$ alkenyl, $C_2$-$C_{10}$ alkynyl, or $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, haloalkyl, cyano, $C_1$-$C_7$ alkoxy; and wherein R⁵ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;

R² is O—Ar, wherein Ar is a fused bicyclic aryl moiety or a monocyclic aryl moiety, either of which aryl moieties is carbocyclic or heterocyclic and is phenyl optionally substituted with a halogen, $C_1$-$C_6$ alkyl, $C_1$-$C_6$ alkoxy;

or R² has the general formula II

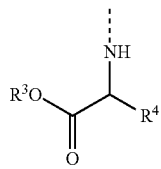

II wherein R¹ and R² can be identical or different;
or R¹ and R² have the general formula III

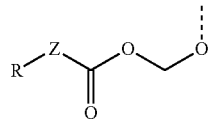

III wherein R¹ and R² can be identical or different;
Z is O;
R is selected from the group consisting of H, aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl;
and/or a pharmaceutical acceptable addition salt thereof and/or a stereoisomer thereof and/or a solvate thereof.

2. The compound according to claim 1, wherein B is selected from the group of adenine, thymine, cytosine and guanine.

3. The compound according to claim 1, wherein R² is O-Ph.

4. The compound according to claim 1, wherein R³ is selected from $C_1$-$C_{10}$ alkyl.

5. The compound according to claim 1, wherein X is $C_1$-$C_{10}$ alkyl and R⁵ is $C_1$-$C_{10}$ alkyl.

6. The compound according to claim 1, wherein R² is O-Ph, and wherein R¹ is selected from the group consisting of

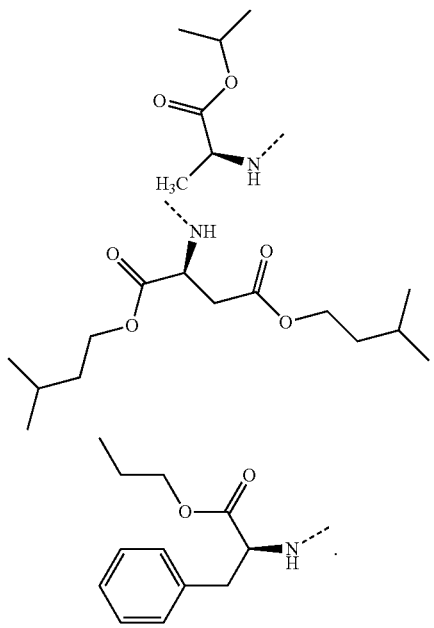

7. The compound according to claim 1, wherein R¹ and R² are identical and are selected from the group consisting of:

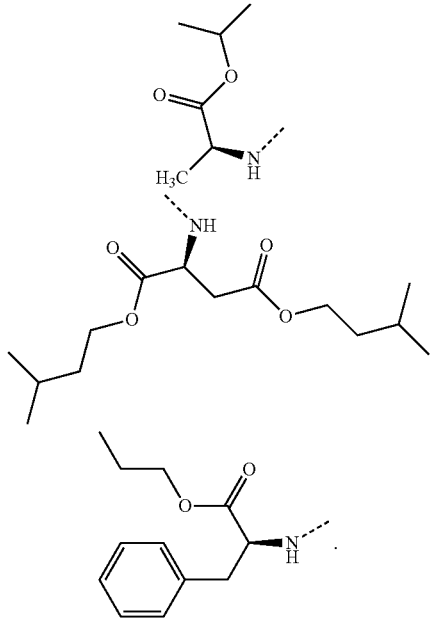

8. A compound selected from the group consisting of:
1'α-(Adenin-9-yl)-2'-deoxy-3'-O-{[N,N'-bis(n-propyl-L-phenylalaninate)]methylphosphonobisamidate}-L-threose;
1'α-(Adenin-9-yl)-2'-deoxy-3'-O-{[N-(isopropyl-L-alaninate)](phenoxy)methylphosphonoamidate]}-L-threose;

1'α-(Adenin-9-yl)-2'-deoxy-3'-O-{[N-(diisoamyl-L-aspartate)](phenoxy)methylphosphonoamidate}-L-threose;

1'α-(Thymin-1-yl)-2'-deoxy-3'-O-[N,N'-bis(n-propyl-L-phenylalaninate)) methylphosphonobisamidate]-threose;

1'α-(Thymin-1-yl)-2'-deoxy-3'-O-{[N-(isopropyl-L-alaninate)](phenoxy)methylphosphonoamidate}-L-threose;

1'α-(Thymin-1-yl)-2'-deoxy-3'-{[N-(diisoamyl-L-aspartate)](phenoxy)methylphosphonoamidate}-L-threose;

1'α-(Cytosin-1-yl)-2'-deoxy-3'-O-{[N,N'-bis(n-propyl-L-alaninate)]methylphosphonobisamidate}-L-threose;

1'α-(Cytosin-1-yl)-2'-deoxy-3'-O-{[N-(isopropyl-L-alaninate)](phenoxy)methylphosphonoamidate}-L-threose;

1'α-(Guanin-9-yl)-2'-deoxy-3'-O-[N,N'-bis(n-propyl-L-phenylalaninate)]methylphosphonobisamidate]-threose;

1'α-(Guanin-9-yl)-2'-deoxy-3'-O-[N,N'-bis(n-propyl-L-alaninate)]methylphosphonobisamidate]-threose;

1'α-(Guanin-9-yl)-2'-deoxy-3'-O-{[N-(isopropyl-L-alaninate)](phenoxy)methylphosphonoamidate}-L-threose, with respectively the following structural formula's:

-continued

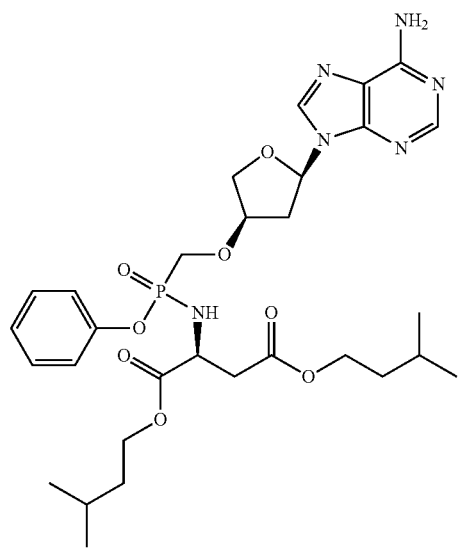

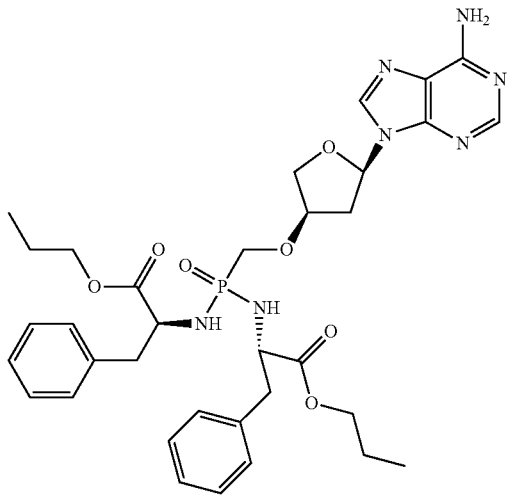

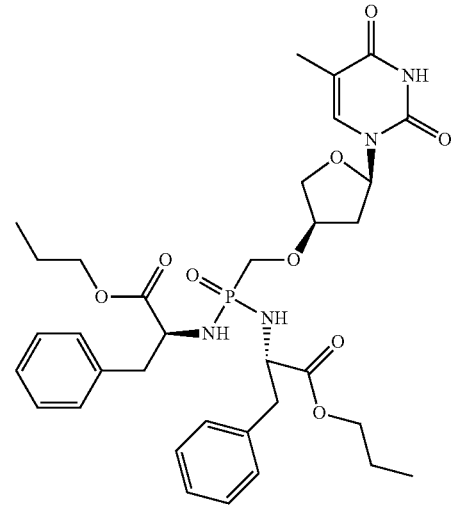

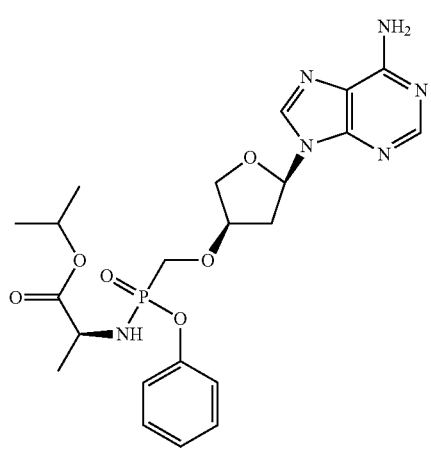

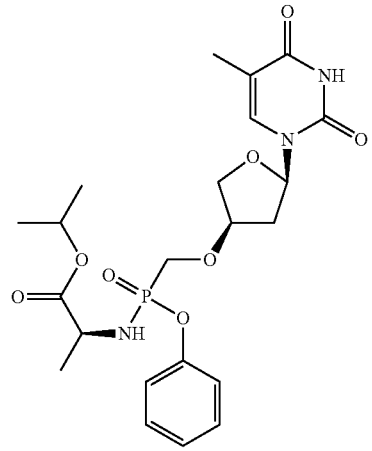

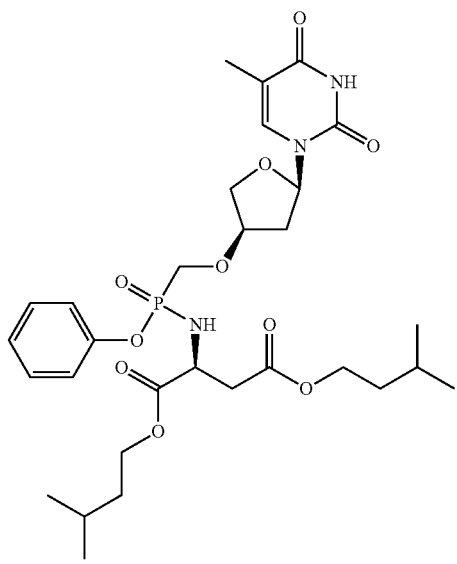

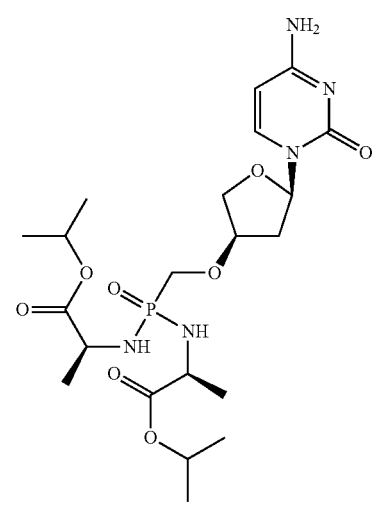

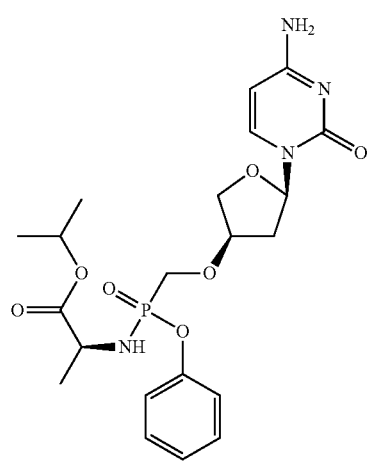

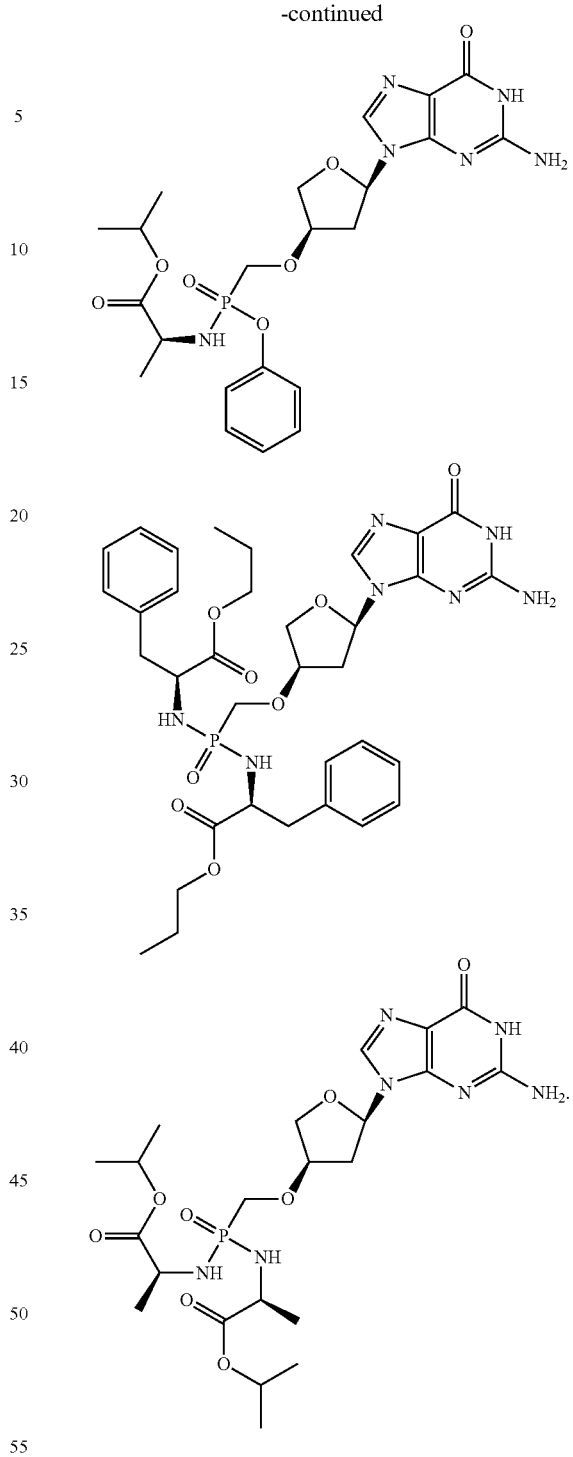

9. A compound according to claim 1 for use as a medicine.

10. A compound according to claim 1 for use as a medicine for the treatment of a viral infection in an animal, mammal or human.

11. The compound according to claim 10, wherein said viral infection is an infection of HBV, HIV, HCV, RSV, dengue virus, influenza virus, CMV, adenovirus, parainfluenza, rhinovirus, BK virus, and/or HSV.

12. A compound according to claim 1 for use as a medicine for the treatment of a proliferative disorder or a cancer in an animal, mammal or human.

13. A pharmaceutical composition comprising a therapeutic amount of a compound according to claim 1 and one or more pharmaceutically acceptable excipients.

14. The pharmaceutical composition according to claim 13, further comprising one or more biologically active drugs being selected from the group consisting of antiviral drugs and/or anti-proliferative drugs.

15. A method of treatment of a viral infection in an animal, mammal or human, comprising the administration of a therapeutically effective amount of a compound according to claim 1, optionally in combination with one or more pharmaceutically acceptable excipients.

16. A method of treatment of a proliferative disorder in an animal, mammal or human, comprising the administration of a therapeutically effective amount of a compound according to claim 1, optionally in combination with one or more pharmaceutically acceptable excipients.

17. A process for preparing a compound according to claim 1, including a step comprising reacting a corresponding nucleoside phosphonate, or a salt thereof, with an amino acid ester represented by the structural formula

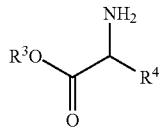

or a salt thereof, and optionally a monocyclic or fused bicyclic aromatic or heteroaromatic hydroxy compound represented by the structural formula HO—Ar.

18. A compound according to claim 8 for use as a medicine.

19. A compound according to claim 8 for use as a medicine for the treatment of a viral infection in an animal, mammal or human.

20. A compound according to claim 8 for use as a medicine for the treatment of a proliferative disorder or a cancer in an animal, mammal or human.

21. A pharmaceutical composition comprising a therapeutic amount of a compound according to claim 8 and one or more pharmaceutically acceptable excipients.

22. The pharmaceutical composition according to claim 21, further comprising one or more biologically active drugs being selected from the group consisting of antiviral drugs and/or anti-proliferative drugs.

23. A method of treatment of a viral infection in an animal, mammal or human, comprising the administration of a therapeutically effective amount of a compound according to claim 8, optionally in combination with one or more pharmaceutically acceptable excipients.

24. A method of treatment of a proliferative disorder in an animal, mammal or human, comprising the administration of a therapeutically effective amount of a compound according to claim 8, optionally in combination with one or more pharmaceutically acceptable excipients.

\* \* \* \* \*